(12) United States Patent
Takizawa et al.

(10) Patent No.: US 7,144,366 B2
(45) Date of Patent: Dec. 5, 2006

(54) CAPSULE MEDICAL APPARATUS HAVING EVACUATION DETECTING AND NOTIFYING DEVICES AND CAPSULE MEDICAL APPARATUS COLLECTING SYSTEM

(75) Inventors: Hironobu Takizawa, Hachioji (JP); Takeshi Yokoi, Hino (JP); Akira Kikuchi, Yokohama (JP)

(73) Assignee: Olympus Corporation, Tokyo (JP)

( * ) Notice: Subject to any disclaimer, the term of this patent is extended or adjusted under 35 U.S.C. 154(b) by 184 days.

(21) Appl. No.: 10/790,263

(22) Filed: Mar. 1, 2004

(65) Prior Publication Data

US 2004/0176685 A1    Sep. 9, 2004

(30) Foreign Application Priority Data

Mar. 4, 2003 (JP) ............................. 2003-057530
May 12, 2003 (JP) ............................. 2003-132999

(51) Int. Cl.
*A61B 1/00* (2006.01)
*A61B 1/04* (2006.01)

(52) U.S. Cl. ...................... 600/117; 600/118
(58) Field of Classification Search ............... 600/109, 600/117, 118, 160, 476
See application file for complete search history.

(56) References Cited

U.S. PATENT DOCUMENTS 5,681,260 A    10/1997    Ueda et al.
6,904,308 B1 *  6/2005    Frisch et al. ............... 600/424
6,939,292 B1 *  9/2005    Mizuno ..................... 600/118
2002/0032366 A1 *  3/2002    Iddan et al. ............... 600/117
2002/0103417 A1 *  8/2002    Gazdzinski ............... 600/109
2002/0173718 A1    11/2002    Frisch et al.
2002/0198470 A1 * 12/2002    Imran et al. ............... 600/587
2003/0020810 A1    1/2003    Takizawa et al.
2003/0023150 A1    1/2003    Yokoi et al.
2003/0114742 A1 *  6/2003    Lewkowicz et al. ........ 600/407
2004/0111011 A1 *  6/2004    Uchiyama et al. ......... 600/160
2004/0210131 A1 * 10/2004    Fukuda et al. ............ 600/424

FOREIGN PATENT DOCUMENTS

| EP | 1 260 176 A2 | 11/2002 |
|---|---|---|
| JP | 61-11107 | 4/1986 |
| JP | 4-8341 | 1/1992 |
| JP | 11-225996 | 8/1999 |
| JP | 2002-556 | 1/2002 |
| JP | 2003-19111 | 1/2003 |
| JP | 2003-38424 | 2/2003 |
| JP | 2003-38425 | 2/2003 |
| WO | WO 03/005877 A2 | 1/2003 |

* cited by examiner

*Primary Examiner*—John Leubecker
*Assistant Examiner*—Philip R Smith
(74) *Attorney, Agent, or Firm*—Scully, Scott, Murphy & Presser, PC

(57) ABSTRACT

A capsule medical apparatus for medical actions such as examination and treatment in the body detects by a sensor or the like whether it is just being evacuated from the body or it has already been evacuated. Upon detecting the capsule medical apparatus is positioned in the large intestine or it has already been evacuated, the capsule medical apparatus notifies such information in association with the detection.

12 Claims, 16 Drawing Sheets

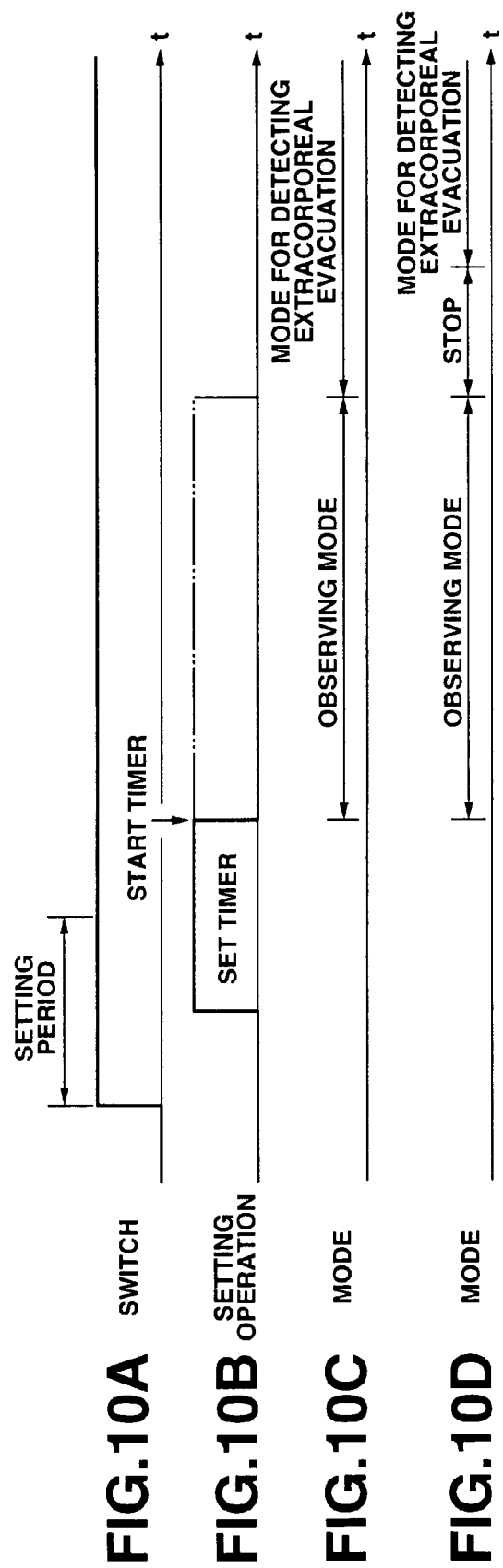

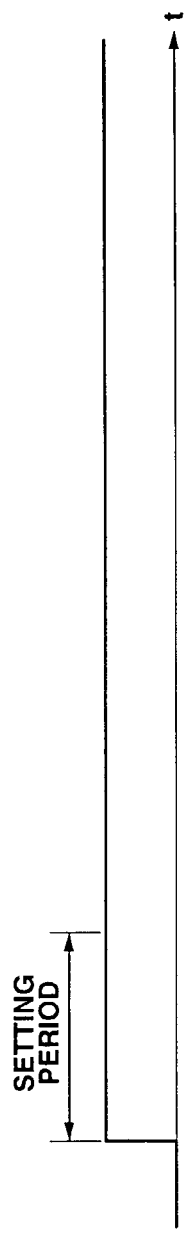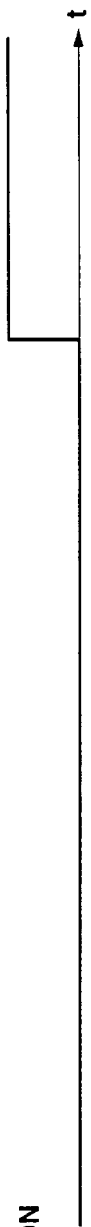
FIG.12A SWITCH
FIG.12B SETTING OPERATION
FIG.12C MODE
FIG.12D pH SENSOR
FIG.12E DETERMINATION OF SENSOR OUTPUT
FIG.12F SETTING OPERATION
FIG.12G MODE

CAPSULE MEDICAL APPARATUS HAVING EVACUATION DETECTING AND NOTIFYING DEVICES AND CAPSULE MEDICAL APPARATUS COLLECTING SYSTEM

This application claims benefit of Japanese Application Nos. 2003-57530 filed on Mar. 4, 2003 and 2003-132999 filed on May 12, 2003, the contents of which are incorporated by this reference.

BACKGROUND OF THE INVENTION

1. Field of the Invention

The present invention relates to a capsule medical apparatus and a capsule medical apparatus collecting system for medical actions such as the examination and treatment of the inside of the body.

2. Description of the Related Art

As is well-known, a method using various examinations such as the complete physical examination and endoscope examination is generally known as a method for checking the health condition of an examinee (patient). Further, a capsule medical apparatus is also well known for easily checking the health condition by swallowing a capsule as a capsule-shaped examining material and by examining in-vivo information. Various above-mentioned capsule medical apparatuses are suggested.

As a first well-known art, Japanese Examined Patent Application Publication No. 61-11107 discloses a medical capsule which is capable of extracting a sample of the body fluid at a predetermined position in the body.

The medical capsule comprises a main body frame including a power circuit and a battery, a sampling collecting cylinder arranged at one end of the main body frame, having an inhaling port, a piston arranged in the sampling collecting cylinder, a compression spring inserted between the piston and the sampling collecting cylinder, a string guide for stopping the piston, and an electric wire which comes into contact with the string guide, and an outer cylinder having an inhaling port which is slidable to the outer periphery of the sampling collecting cylinder.

In the examination using the above-mentioned medical capsule, a patient first swallows the medical capsule, and electric waves are emitted to the medical capsule by an extracorporeal device when the medical capsule reaches the organ of digestion. The electric waves are generated, then, the power circuit in the main body frame operates, and current flows to the electric wire. Further, the string guide contact with the electric wire is melted and cut. The string guide is cut and then the stop operation of the piston is released. Thus, the piston moves by the force of the compression power. The body fluid around the outer cylinder is obtained from the inhaling port of the sampling collecting cylinder which matches the outer cylinder. Further, the movement of the piston slides the outer cylinder and the inhaling port of the sampling collecting cylinder does not match the outer cylinder, then the sampling collecting cylinder is closed, and the body fluid can be obtained in the sampling collecting cylinder.

After the medical capsule is evacuated from the body and is collected, the obtained body fluid is picked up from the sampling collecting cylinder and is analyzed and examined.

As a second well-known art, Japanese Unexamined Patent Application Publication No. 11-225996 discloses a capsule living body information examining apparatus which can detect living body information such as video body information. The capsule living body information examining apparatus has a light output port which outputs illumination light to the living body, an image pick-up port which picks up an image of the living body, and a casing having a living body information sensor which detects the temperature of the living body. The casing includes a battery which supplies power to the components, a white LED which illuminates the living body via the light output port, a CCD which picks up an image of the living body via the image pick-up port, a control circuit which controls the above-mentioned components, and a memory which stores the living body information that is obtained from the components. The white LED also functions as transmitting means which externally transmits the living body information stored in the memory.

In the examination using the capsule living body information examining apparatus, the patient turns on a power switch, and swallows the capsule living body information examining apparatus. The swallowed capsule living body information examining apparatus moves in the organ in the living body and the white LED illuminates the body. Then, the CCD picks up images of portions. The image pick-up information is stored in the memory. Further, the information obtained by the living body information sensor is stored in the memory.

As described above, the capsule living body information examining apparatus which detects the living body information of the portions in the body is evacuated and collected. After that, the information stored in the memory via the white LED is extracted and is analyzed and examined.

SUMMARY OF THE INVENTION

According to the present invention, a capsule medical apparatus for medical actions such as examination and treatment in the body, comprises:

a detecting device which detects whether the capsule medical apparatus is just being evacuated from the body or it has already been evacuated; and a notifying device which extracorporeally notifies the detected result in association with the detecting device.

BRIEF DESCRIPTION OF THE DRAWINGS

FIGS. 1A to 8 relate to a first embodiment of the present invention,

FIG. 1A is a diagram showing, as a using example, the configuration of a capsule endoscope apparatus according to the first embodiment of the present invention;

FIG. 2 is a diagram showing the internal configuration of a capsule endoscope;

FIG. 3 is a diagram showing two modes forming an operating mode;

FIGS. 4A to 4E are timing charts showing operating examples in an observing mode;

FIGS. 5A to 5G are timing charts showing typical operating examples in the operation mode;

FIGS. 6A to 6H are timing charts showing typical operating examples in the operation mode when a timer starts;

FIG. 7 is a diagram showing the configuration of a capsule according to a first modification of the first embodiment;

FIG. 8 is a diagram showing the configuration of a capsule according to a second modification of the first embodiment;

FIGS. 9 to 10D relate to a second embodiment of the present invention,

FIG. 9 is a diagram showing the configuration of a capsule medical apparatus according to the second embodiment of the present invention;

FIGS. 10A to 10D are timing charts showing typical operating examples;

FIGS. 11 to 12G relate to a third embodiment of the present invention,

FIG. 11 is a diagram showing the configuration of a capsule medical apparatus according to the third embodiment of the present invention;

FIGS. 12A to 12G are timing charts showing typical operating examples;

FIG. 13 is a conceptual diagram showing a capsule endoscope collecting system and a capsule endoscope according to the fourth embodiment of the present invention;

FIG. 14 is a cross-sectional view of the capsule endoscope shown in FIG. 13;

FIG. 15 is a diagram showing the configuration of an extracorporeal device of the capsule endoscope collecting system shown in FIG. 13;

FIG. 16 is a flowchart showing the operation in the case of collecting the capsule endoscope by using the capsule endoscope collecting system shown in FIG. 13;

FIG. 17 is a conceptual diagram showing a capsule endoscope collecting system and a capsule endoscope according to the fifth embodiment of the present invention;

FIG. 18 is a cross-sectional view showing the capsule endoscope shown in FIG. 17;

FIG. 19 is a diagram showing the configuration of an extracorporeal device of the capsule endoscope collecting system shown in FIG. 17;

FIG. 20 is a conceptual diagram showing a capsule endoscope collecting system and a capsule endoscope according to the sixth embodiment of the present invention;

FIG. 21 is a cross-sectional view showing the capsule endoscope shown in FIG. 20;

FIG. 22 is a diagram showing the configuration of an extracorporeal device of the capsule endoscope collecting system shown in FIG. 20; and FIG. 23 is a flowchart showing the operation in the case of collecting the capsule endoscope by using the capsule endoscope collecting system shown in FIG. 20.

DESCRIPTION OF THE PREFERRED EMBODIMENTS

Hereinbelow, a description is given of embodiments of the present invention with reference to the drawings.

(First Embodiment)

A first embodiment of the present invention will be described with reference to FIGS. 1A to 8.

Figure 1B:
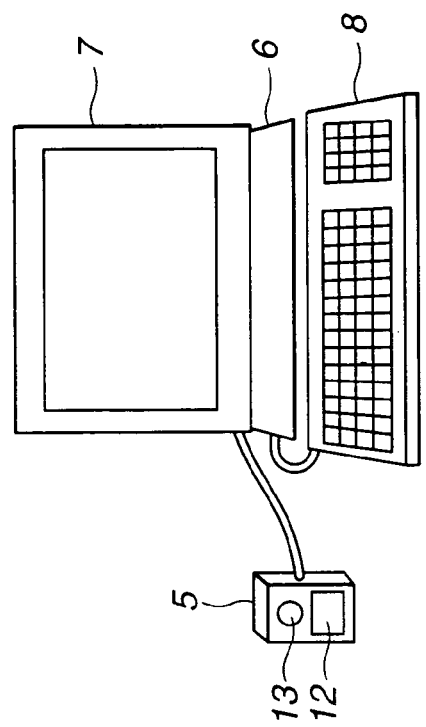
FIG. 1B is a diagram showing a personal computer to which an extracorporeal unit is connected.
Figure 1A:
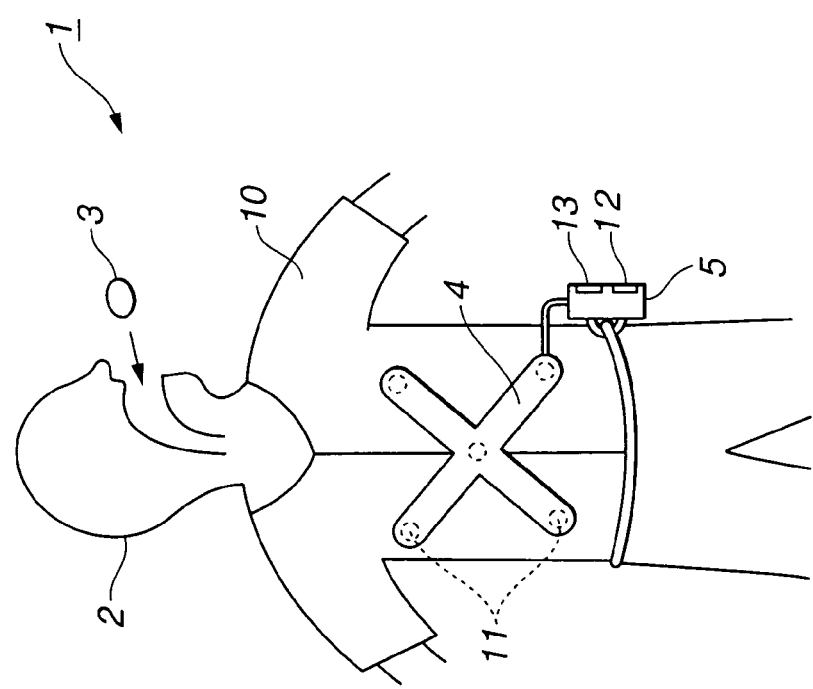

Referring to FIG. 1A, according to the first embodiment of the present invention, as a capsule medical apparatus which is swallowed from the mouth of a patient 2 thus to transmit by radio an image signal obtained by optically picking up an image of a wall surface in the luminal portion in the body cavity upon the passage therethrough, a capsule medical system 1 comprises a capsule endoscope (hereinafter, abbreviated to a capsule except for other similar cases) 3, an antenna unit 4 which is extracorporeally arranged to the patient 2, and which receives the image signal transmitted by the capsule 3, and an extracorporeal unit 5 which is extracorporeally arranged to the patient 2 and which has a function for receiving the image signal received via the antenna unit 4 and for storing the image.

Referring to FIG. 1B, the extracorporeal unit 5 is detachably connected to a personal computer (hereinafter, abbreviated to a PC) 6, captures the image stored in the extracorporeal unit 5 by the PC 6, stores the captured image in a hard disk, and displays the stored image on a display unit 7. A keyboard 8 for inputting data and the like is connected to the PC 6.

Referring to FIG. 1A, when the patient 2 swallows the capsule 3 and the endoscope examination is used as a medical action, a plurality of antennas 11 are attached to the antenna unit 4, and the antenna unit 4 is attached to a shirt 10 worn by the patient 2. An image signal is picked up by the capsule 3 is transmitted from the antennas 11 built in the capsule 3 and is received by the antenna unit 4. The extracorporeal unit 5 connected to the antenna unit 4 stores the picked-up image. The extracorporeal unit 5 is attached to a belt of the patient 2 by a detachable hook. Further, the extracorporeal unit 5 is box-shaped and has a liquid crystal monitor 12 for displaying the image in front thereof and an operating button 13 for operation.

Figure 2:
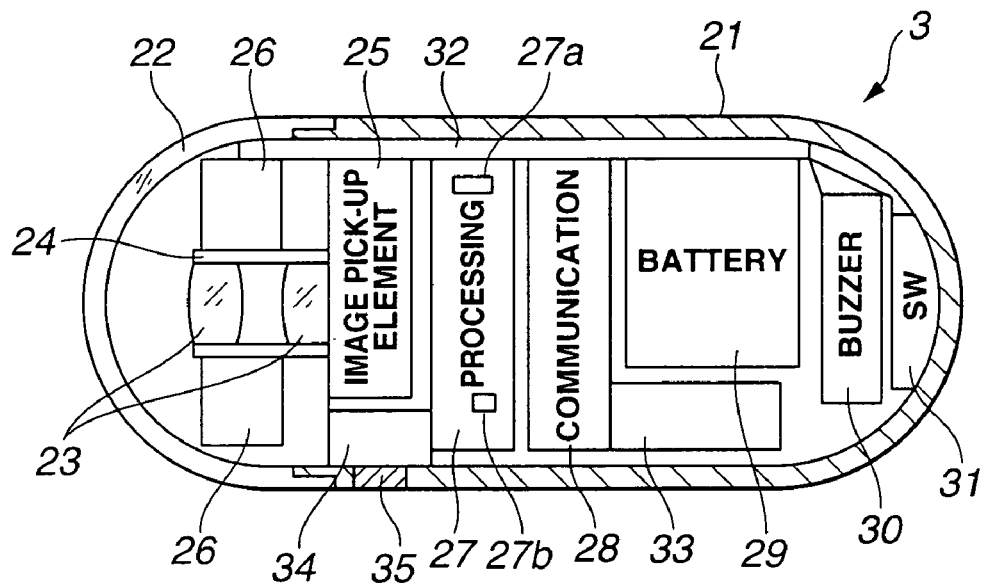

Referring to FIG. 2, the capsule 3 has an exterior container which has therein the watertight structure. The exterior container includes a main body 21 which is cylindrical-shaped and is closed at one opening end thereof with semi-spherical shape and a semi-spherical transparent cover 22 which is fit and fixed to the other opening end of the main body 21. An image pick-up element 25 for picking up an image such as a COMS imager is arranged at the image forming position.

In the center of the inner side of the transparent cover 22 in the exterior container, an objective lens 23 for forming an optical image of an observing target is attached to a lens frame 24.

Further, plurality of white LEDs 26 as illuminating devices are arranged around the objective lens 23.

The image pick-up element 25 has, on the back side thereof, a processing circuit 27 which drives the white LEDs 26, drives the image pick-up element 25, and performs the signal processing and controlling of the image pick-up element 25, a communication circuit 28 which transmits, to the extracorporeal unit 5, the image signal picked up by the image pick-up element 25 and demodulates the signal transmitted from the extracorporeal unit 5, a battery 29 which supplies power for operation to the circuits, a buzzer circuit 30 as sound notifying means for notifying, and a switch 31 which switches on and off the battery 29. The processing circuit 27 includes a CPU 27a which performs the control operation and a timer 27b for time counting.

The main body 21 has, in the longitudinal direction thereof, a flexible printed circuit board (hereinafter, abbreviated to an FPC) 32. The FPC 32 is electrically connected to the image pick-up element 25, the processing circuit 27, the communication circuit 29, the battery 29, the buzzer circuit 30, and the switch 31.

An antenna 33 for receiving and transmitting a signal by radio waves from/to the extracorporeal unit 5 is connected to the communication circuit 29.

The capsule 3 according to the first embodiment includes a temperature sensor 34 which detects that the capsule 3 is extracorporeally evacuated. A signal detected by the temperature sensor 34 is supplied to the buzzer circuit 30 via the FPC 32 so as to drive a buzzer of the buzzer circuit 30.

A temperature detecting surface of the temperature sensor 34 is contact with the side inner-surface of the main body 21. Further, the side-surface portion of the temperature sensor 34 is locally made of a member 35 such as metal having a higher thermal conductivity. The temperature sensor 34 detects, via the member 35, the temperature when the capsule 3 is evacuated from the body inside to the outside, namely, the temperature further lower than that of the body inside. Thus, the temperature sensor 34 drives the buzzer circuit 30 for notification by sound.

The capsule 3 according to the first embodiment illuminates and picks up the image, that is, observes the body inside in the case of switching on the switch 31 and enters a an observing mode (as an operating mode) for the medical action of the capsule 3 which transmits the image pick-up signal to the extracorporeal unit 5 side.

The capsule 3 according to the first embodiment has a standby mode as well as the observing mode. In the standby mode, the temperature sensor 34 detects whether or not the capsule 3 is extracorporeally evacuated.

Figure 3:
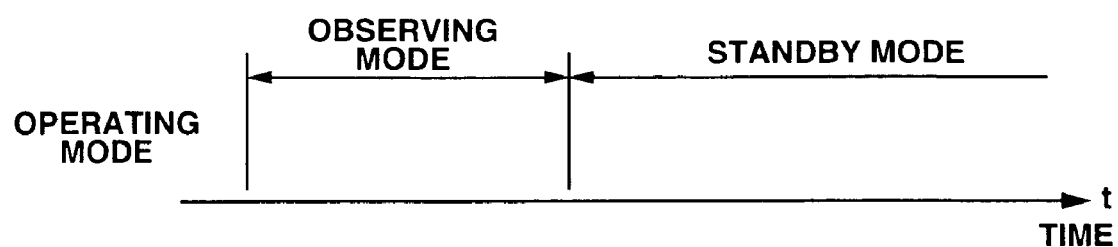
Figure 4:
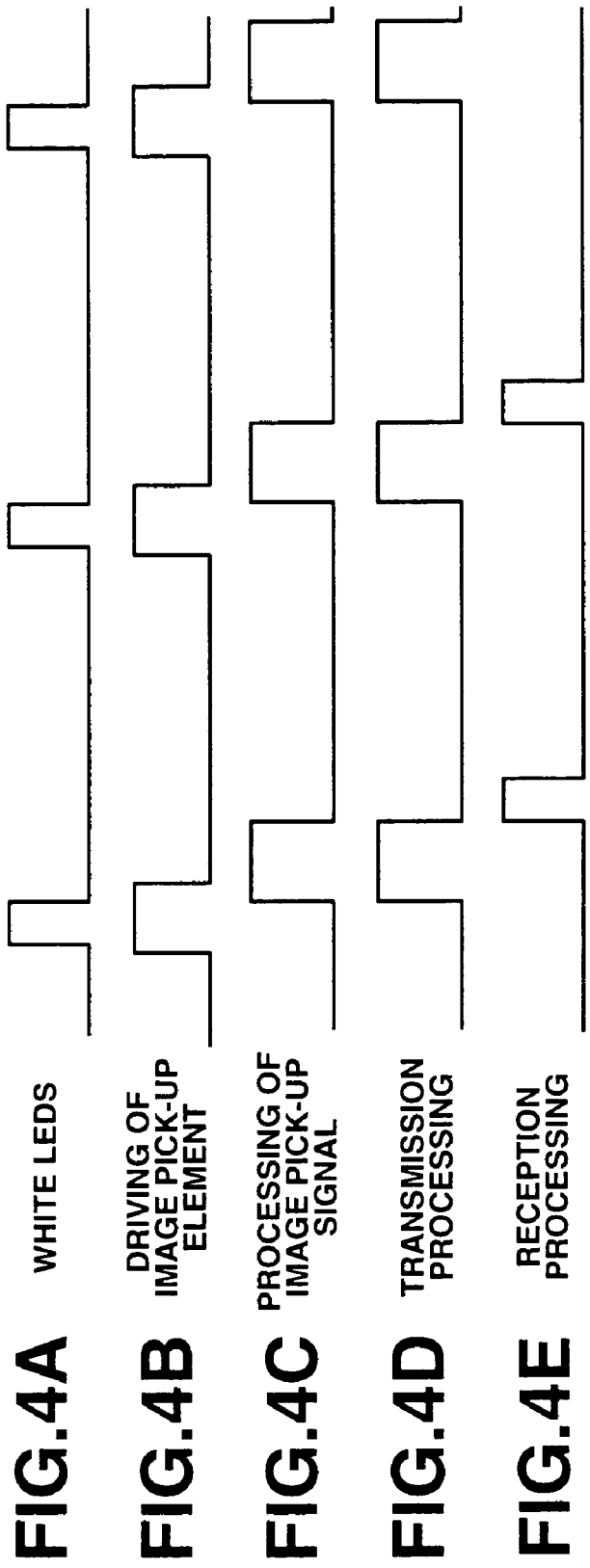

That is, referring to FIG. 3, the capsule 3 according to the first embodiment has both the observing mode and the standby mode.

Referring to FIGS. 4A to 4E, the processing for the illumination and image pick-up operation is intermittently performed in the observing mode.

Referring to FIG. 4A, the white LEDs 26 emit light pulses at the period of approximately one second. During the illuminating period for the light emission, the image pick-up element 25 picks up the image by an image pick-up portion (refer to FIG. 4B), and intermittently performs the driving of the signal transfer of the image pick-up element 25 synchronously with a timing for stopping the light emission, the image pick-up signal processing for the image pick-up signal outputted from the image pick-up element 25, and the extracorporeal transmission processing using the communication circuit 28 (refer to FIGS. 4C and 4D).

In the observing mode, the communication circuit 28 performs the reception processing for switching to the reception, for receiving a signal transmitted from the body outside for a short period after the transmission processing, and for determining whether or not a predetermined signal is detected (refer to FIG. 4E).

In the receiving mode, a mode switching signal is received from the body outside, then, the detecting signal is transmitted to the CPU forming the processing circuit 27. The CPU ends the processing in the observing mode, and performs the control processing through which the observing mode changes to the standby mode. Incidentally, the temperature sensor 34 does not detect the temperature in the observing mode. Further, the buzzer circuit 30 does not operate in the observing mode.

Therefore, the capsule 3 observes the body inside through the illumination and the image pick-up operation in the observing mode. When it is obvious that the observation at the portion as the examining target ends, the operating button 13 of the extracorporeal unit 5 is operated and thus a signal for setting the standby mode is transmitted so as to set the standby mode.

According to the first embodiment, in the case of setting the standby mode, the operating mode can be selected and set in accordance with the proper time sequence depending on the examining status, for example, the standby mode is promptly set in response to a mode changing instruction, or the standby mode is set just after timer setting time by starting the timer depending on the status.

Figure 5:
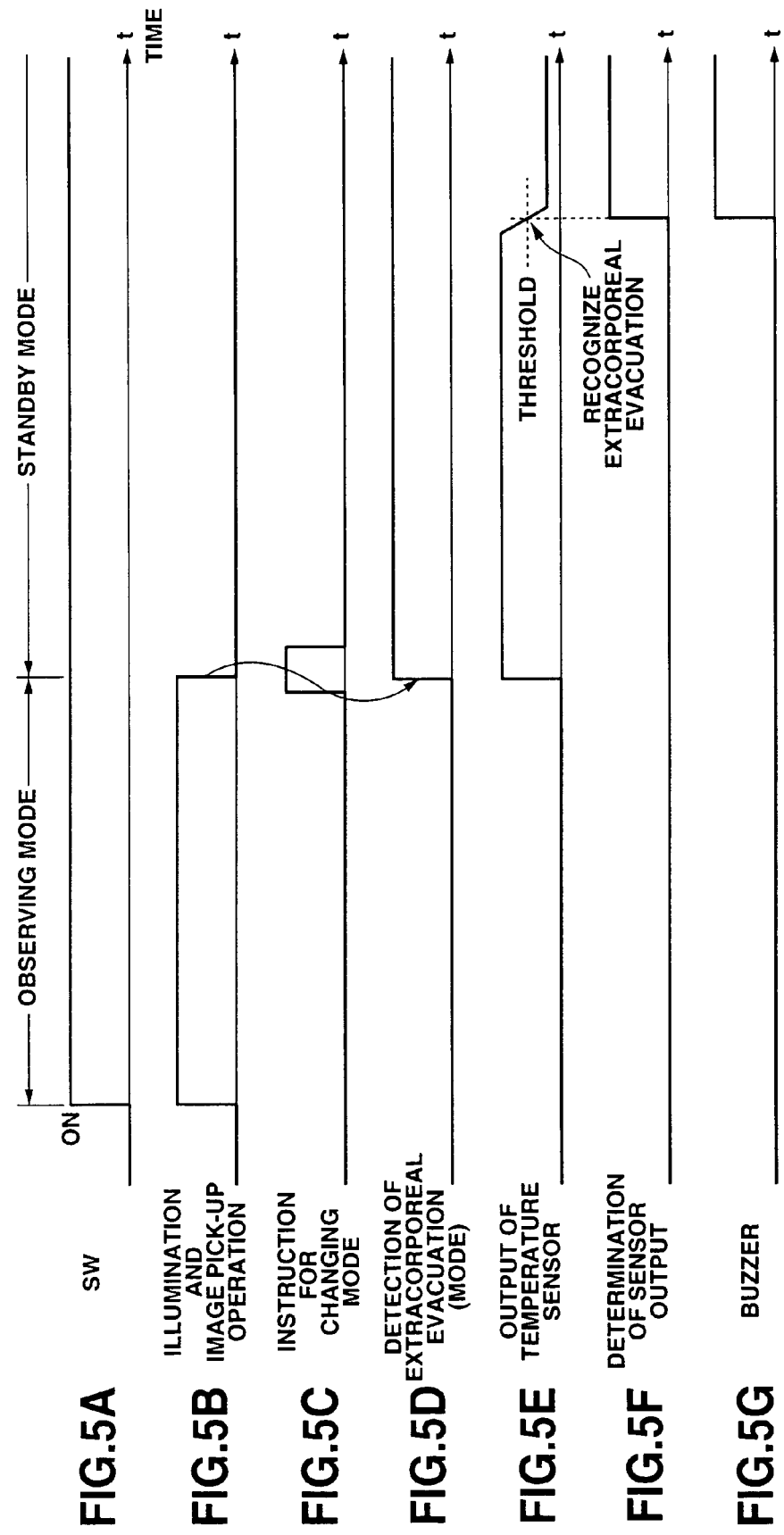
Figure 6:
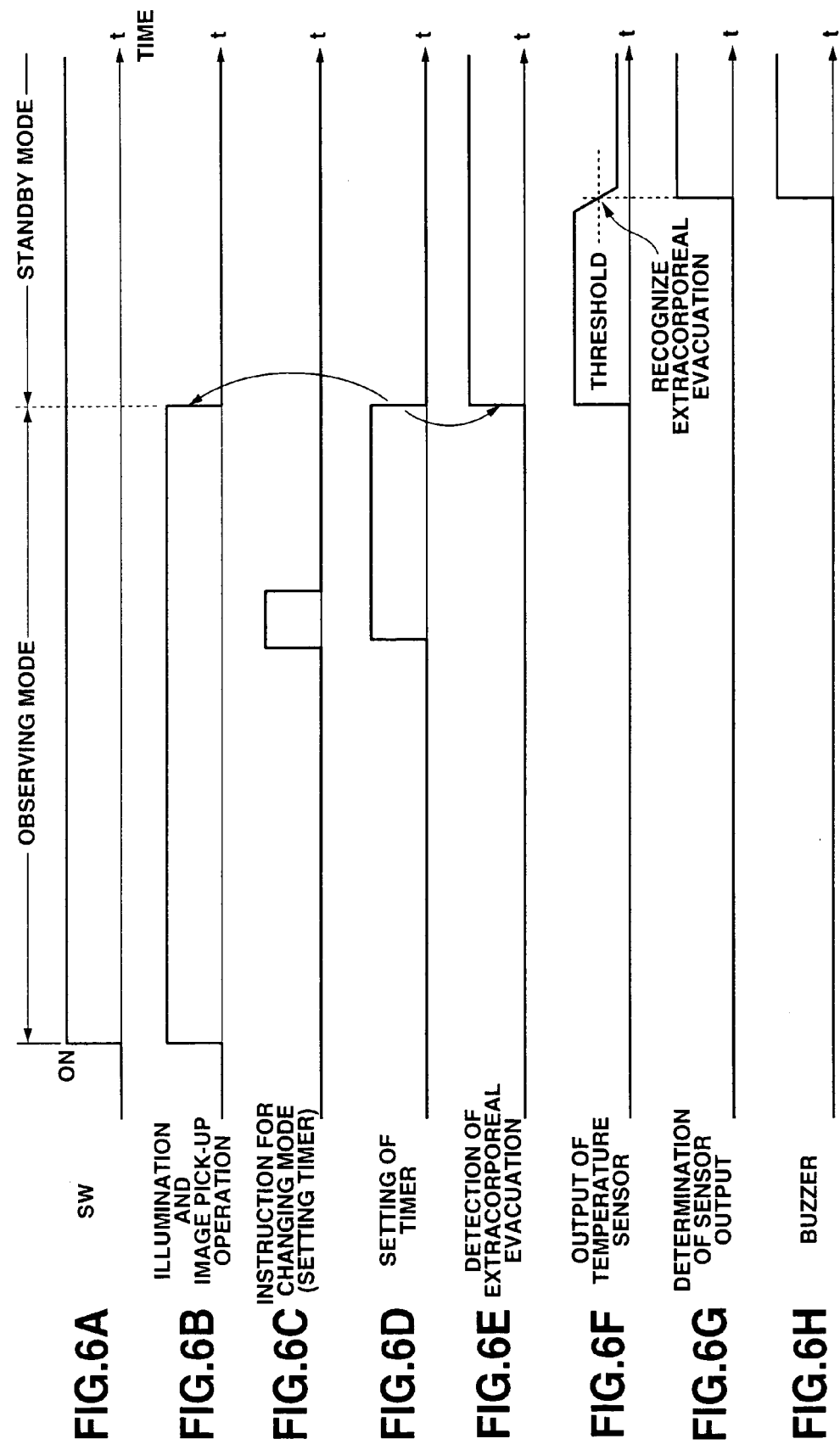

Next, the operation according to the first embodiment will be described with reference to FIG. 5. First, a description is given of the case of detecting that the capsule 3 is extracorporeally evacuated in the entire standby mode (the detection of the extracorporeal evacuation).

Referring to FIG. 5A, the patient 2 turns on the switch 31 of the capsule 3 and swallows the capsule 3. By switching on the switch 31, power for operation is supplied to the processing circuit 27 and the mode enters the observing mode. As shown in FIG. 4A, the white LEDs 26, the image pick-up element 25, and the like are intermittently driven in the observing mode, and the processing circuit 27 performs the signal processing of the image pick-up signal outputted from the image pick-up element 25. Further, the communication circuit 28 transmits the signal from the antenna 33 to the outside by radio waves. Referring to FIG. 5B, the operating status shown in FIG. 4A is simply shown as the result of the illumination and the image pick-up operation.

The extracorporeal unit 5 receives the signal transmitted by the radio waves and the liquid crystal monitor 12 displays the signal. By using the image displayed on the liquid crystal monitor 12, an operator can schematically determine where the capsule 3 passes in the body of the patient 2.

In the case of determining the end of the image pick-up operation of the portion as the examining target, a predetermined key of the operating button 13 is operated and the mode change instructing signal is transmitted to the capsule 3 from the extracorporeal unit 5 as shown in FIG. 5C.

The capsule 3 stops the illumination and image pick-up operation at the timing at which the mode change instructing signal is actually received. The capsule 3 enters the standby mode for the detection of the extracorporeal evacuation (indicating the status by the H level as shown in FIG. 5D), namely, for detecting whether or not the capsule 3 is extracorporeally evacuated as a result of the temperature detection using the temperature sensor 34.

As a result of the switching, the illumination with large energy consumption is prevented and, consequently, the operation for the temperature detection can be performed for a long time.

Referring to FIG. 5E, in the temperature detecting mode, the temperature sensor 34 enters the operating status and sends an output from the temperature sensor 34 to a sensor output determining circuit. The capsule 3 is extracorporeally evacuated and, then, the temperature is highly reduced as compared with that of the body. Thus, the sensor output determining circuit compares the temperature with a threshold so as to recognize (determine) the extracorporeal evacuation of the capsule 3.

An extracorporeal determining signal indicating the extracorporeal evacuation is outputted as shown in FIG. 5F. Referring to FIG. 5G, the buzzer notifies by sound the extracorporeal evacuation of the capsule 3 to the patient 2.

As mentioned above, the capsule 3 is extracorporeally evacuated and then the status is notified by the sound. Therefore, the patient 2 and the like can promptly know that the capsule 3 is extracorporeally evacuated. Thus, the capsule 3 may be collected by a collecting tool (not shown) having, at the end thereof, magnet for absorbing a magnetic member forming the battery 29 of the capsule 3.

According to the first embodiment, different from the case wherein the extracorporeal evacuation of the capsule 3 is not notified because of no function of the detection, the capsule 3 may be collected because the notifying means notifies the extracorporeal evacuation of the capsule 3. Thus, the capsule 3 can accurately be collected without its losing. The use of the collecting tool facilitates the collection of the capsule 3.

Next, a description is given of typical examples of the operation for starting the timer and setting the mode to the standby one after the time set by the timer with reference to FIGS. 6A to 6H.

First, referring to FIG. 6A, the switch 31 is turned on similarly to the case shown in FIG. 5A, thus, the observing mode is set, and the patient 2 swallows the capsule 3. Referring to FIG. 6B, the illumination and image pick-up operation are performed in the observing mode. Since it is an excessive load for medical staffs, e.g., operator to continuously monitor the passage status of the capsule 3 which is swallowed by the patient 2, the status is sometimes observed on the liquid crystal monitor 12.

The image enables the estimation of the approximate end time for observing the desired portion at the proper time. Then, the mode is changed, thus to set a bit longer time than the estimation time to the end time of the observing mode.

That is, the mode change is instructed by operating the operating button 13, and the time for actually starting the instructing signal (the above-mentioned end time) is inputted to transmit the time to the capsule 3 (refer to FIG. 6C).

The capsule 3 receives the instructing signal, then, the contents of the instructing signal are returned to the extracorporeal unit 5, and the transmitted contents are displayed on the liquid crystal monitor 12. The medical staff confirms whether or not the contents are correct and, if they are correct, the OK operation is transmitted whereupon the capsule 3 sets the sequential time of the observing mode to the timer 27b of the processing circuit 27.

Referring to FIG. 6D, the timer setting is shown. The capsule 3 continues the observing mode and notifies the CPU 27a in the processing circuit 27 of the end time set by the timer 27b. In response to the notification, the CPU 27a stops the illumination and image pick-up operation. The mode is changed to the standby one as the mode for detecting the extracorporeal evacuation (indicating the H level in FIG. 6E), in which the capsule 3 is extracorporeally evacuated based on the temperature detection of the temperature sensor 34. The subsequent operation is shown in FIGS. 6F to 6H, that is, similar to those shown in FIGS. 5E to 5G.

As mentioned above, the timer 27b is started, thus, the standby mode is set after the setting time of the timer 27b, and the extracorporeal evacuation of the capsule 3 is detected.

According to the first embodiment, a predetermined medical action (optical observation in the body) is performed in the observing mode as the operating mode. Further, after ending the medical action, it is possible to set the mode for ending the medical action and extracorporeally evacuating the capsule 3, in which it is detected whether or nor the capsule 3 is extracorporeally evacuated. The extracorporeal evacuation of the capsule 3 is detected and such information is detected based on the output and is notified by the buzzer as the notifying means and therefore the capsule 3 extracorporeally evacuated is collected without fail.

Figure 7:
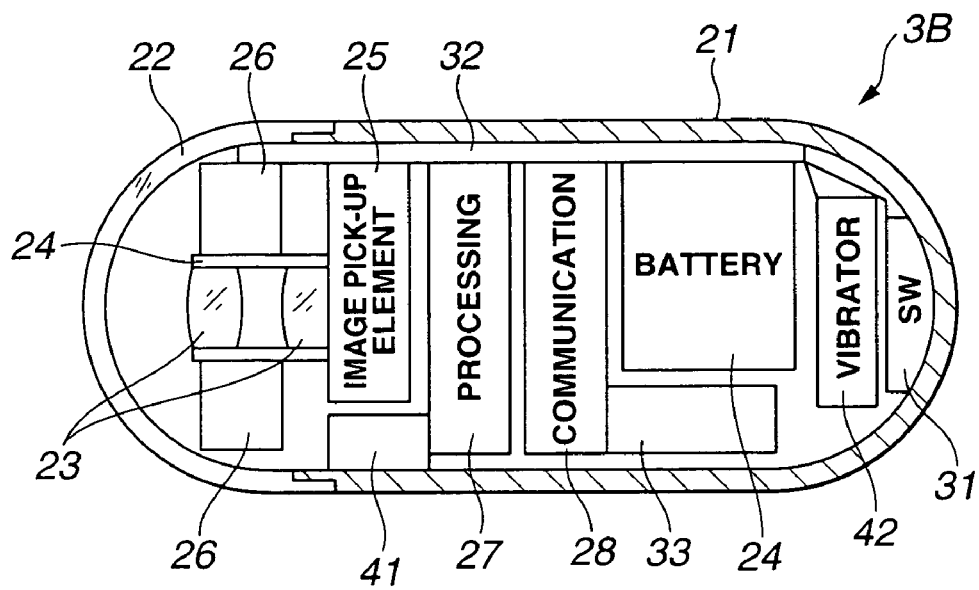

FIG. 7 shows the configuration of a capsule 3B according to a first modification of the first embodiment. The capsule 3B uses an optical sensor 41 in place of the temperature sensor 34. As the notifying means, a vibrator 42 such as a vibrating motor, vibrator, or ultrasonic vibrator is used in place of the buzzer.

The optical sensor 41 has a surface on a transparent cover side as a light receiving surface. The structures of the detecting means and the notifying means are different from those according to the first embodiment. However, the operations of the detecting means and the notifying means are almost the same as those in the capsule 3. Other structures are the same as those shown in FIG. 2. In FIG. 7, the CPU 27a and the timer 27b in the processing circuit 27 are omitted (also in FIG. 8). Advantages according to the first modification are the same as those in the capsule 3 shown in FIG. 2.

As another modification of the first one shown in FIG. 7, the image pick-up element 25 may be used as the optical sensor without the optical sensor 41. In this case, costs are reduced.

Figure 8:
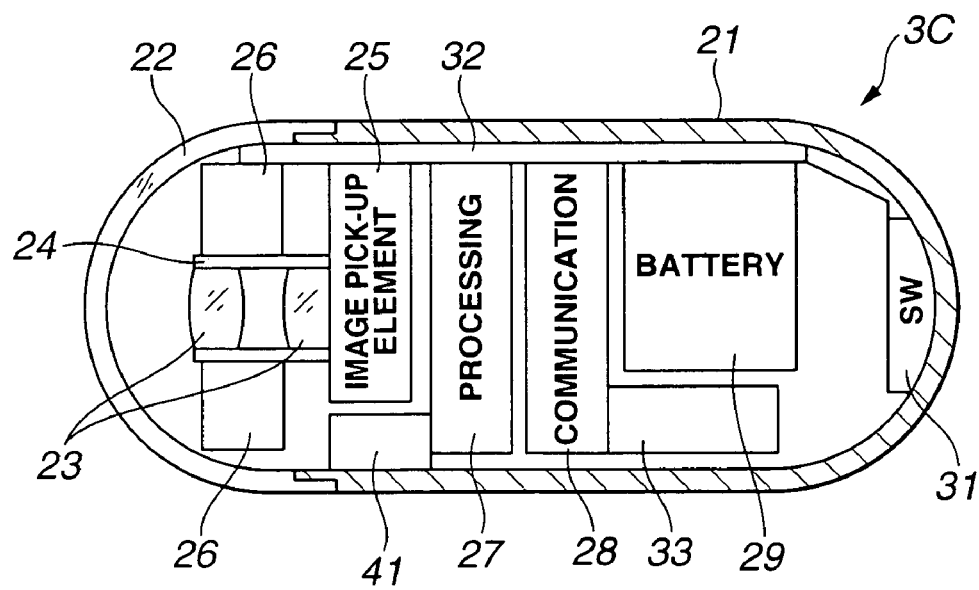

FIG. 8 shows the configuration of a capsule 3C according to a second modification of the first embodiment. The capsule 3C uses the white LED 26 as the notifying means using light, in place of the vibrator 42. When the white LED 26 emits light upon notifying, pulse light is intermittently emitted at a time interval longer than the photographing time, and the notification is sent to the user by using the light with the saved consumption of energy.

The operation according to the second modification is the same as that of the capsule 3. According to the second modification, the white LED 26 is commonly used for the illumination for the image pick-up operation and for the light emission for notifying the extracorporeal evacuation. Therefore, advantageously, the costs of the capsule 3C are reduced.

In the case of using illuminating means which picks up a color image by combining devices for light emission of R, G, and B wavelengths, in place of the white LED 26, the light emission may be performed with light having specific wavelengths of the devices.

(Second Embodiment)

Figure 9:
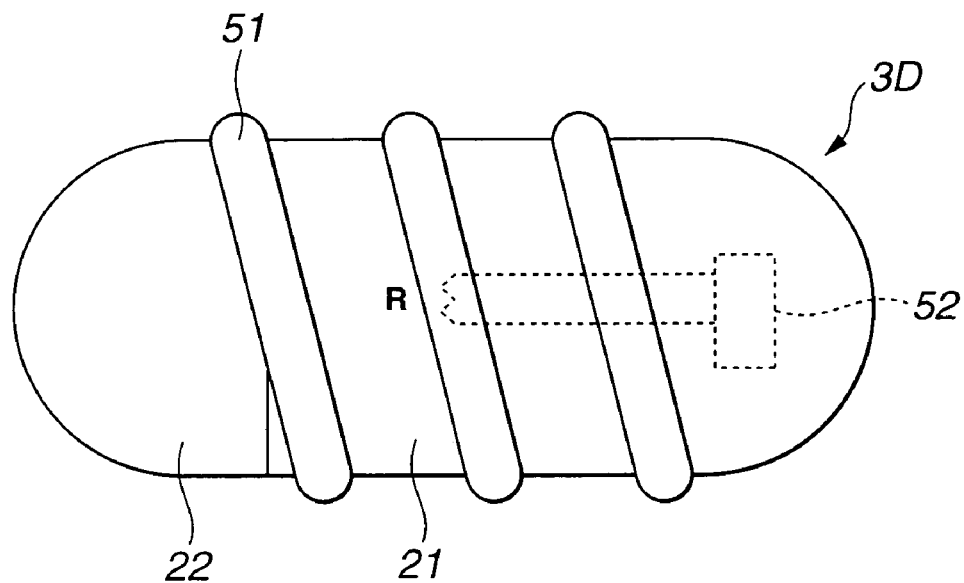

Next, a second embodiment of the present invention will be described with reference to FIG. 9. FIG. 9 shows a capsule 3D according to the second embodiment of the present invention. The capsule 3D has spiral projections 51 on the outer peripheral surface of the main body 21, in place of the optical sensor 41 in the capsule 3C shown in FIG. 8. The projections 51 are made of elastic rubber having the conductivity. The elastic rubber is compared with the standard resistance by a resistance detecting circuit 52 arranged in the capsule 3D via the contact on the inner surface side.

That is, as schematically shown in FIG. 9, the elastic rubber forming the projections 51 functions as a resistor R. When the elastic rubber is compressed and modified by pressure generated by the body wall, the level of the resistor R drops. Therefore, when the elastic rubber is evacuated and is not compressed, the level of the resistor R increases. By comparing the reference level of the resistor R with that slightly lower than the resistance when the elastic rubber is extracorporeally evacuated, the extracorporeal evacuation of the capsule 3D can be detected. An output of the detection results in flickering the white LED 26 and in notifying the evacuation.

In this case, it is assumed that the time interval, at which the level of the resistor R is higher than the reference resistance Rs, continues more than the reference time which is set to be longer than the period of the peristaltic movement of the body, the capsule 3D is extracorporeally evacuated, the notifying means may be set. Alternatively, in the case of the detecting the pulsation pressure, it is determined that the capsule 3D exists in the body. In the case of detecting no pulsation pressure, it may be determined that the capsule 3D exists outside the body and the notifying means may notify the extracorporeal evacuation of the capsule 3D.

According to the second embodiment, the switch 31 is first turned on and then the mode enters the setting mode for selecting the operating mode (or setting period). Therefore, in the setting mode, the operating mode can be set. For example, after turning on the switch 31, the capsule 3D receives an extracorporeal signal for a predetermined time. If a preset signal is received, the mode enters one corresponding to the signal. On the other hand if the preset signal is not received for the predetermined time, the setting is performed so that the mode enters the normal observing mode, the observing mode set by a default, or the mode for detecting the extracorporeal evacuation (processing is implemented by the CPU 27a in the processing circuit 27).

Depending on the using case, the operating mode is selected and set. For example, upon setting the time for the observing mode (changing the observing time different from that set by the default), the operating button 13 is operated, thus to set the time for the observing mode by using the timer 27b. The mode is set to the observing one for the time set by the timer 27b. Thereafter, the mode shifts to the detecting mode of the extracorporeal evacuation of the capsule 3D.

The operation in this case is basically the same as the operation which is first set by the timer 27b with reference to the timing chart shown in FIGS. 6A to 6H. According to the second embodiment, in the observing mode, the instructing signal is transmitted, thereby starting the timer 27b and changing the time for the observing mode.

FIGS. 10A to 10D show typical examples of the operation according to the second embodiment.

When the switch 31 is turned on, the timer 27b is started, and the observing mode is executed for a proper time, the operating button 13 is operated before the setting period passes after turning on the switch 31 shown in FIG. 10A. Then, an instruction for setting the operating mode is sent to the capsule 3D. Further, the time for the observing mode using the timer 27b is inputted and a return key or the like is pressed (the operation is shown as the operation for setting the timer 27b in FIG. 10B).

After the instruction, referring to FIG. 10C, the capsule 3D operates in the observing mode for the setting time and then in the mode for detecting the extracorporeal evacuation.

According to the second embodiment, when any time is required until the capsule 3D is extracorporeally evacuated after observing the periphery of the target portion in the body, the observing mode is stopped and the time is simply measured without detecting the extracorporeal evacuation. Then, after the setting time passes, the mode can be set to the mode for detecting the extracorporeal evacuation. FIG. 10D shows an example of the operation in this case. The setting of the operation can first be performed and, alternatively, it can be performed in the halfway of the observing mode.

According to the second embodiment, the operating mode can first be set depending on the using status for the medical action such as the examination using the capsule 3D. Further, the mode can be changed even in the halfway, and the capsule 3D can be applied to various fields. Similarly to the first embodiment, the extracorporeal evacuation is detected after using the capsule 3D in the medical action, the notifying means can notify the detection.

It is detected whether or not the capsule 3D is extracorporeally evacuated by detecting the resistance as shown in FIG. 9, it may be detected whether or not the extracorporeal evacuation of the capsule is detected by using a pressure sensor.

(Third Embodiment)

Figure 11:
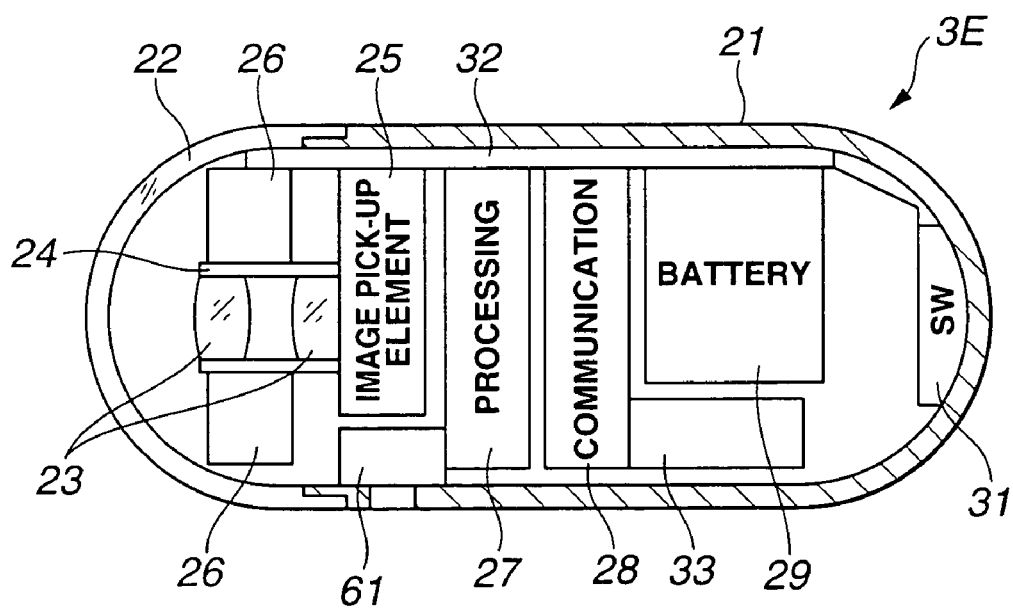

Next, a description is given of a third embodiment of the present invention with reference to FIG. 11. FIG. 11 shows a capsule 3E according to the third embodiment. The capsule 3E uses a pH sensor 61, in place of the optical sensor 41 in the capsule 3C shown in FIG. 8. Further, a part of the pH sensor 61 surface is exposed to the outer surface so as to detect pH of an external portion of the capsule 3E.

As described above according to the second embodiment, the user turns on the switch 31 to set the operating mode. When the examining target portion is the small intestine, it is determined (detected or recognized) that the setting medical action is completed upon detecting pH at the portion corresponding to the large intestine on the bottom of the small intestine, the observing mode as the originally main medical action is stopped and, for example, the notifying means using the white LEDs 26 is started.

Therefore, in the observing mode according to the third embodiment, the image pick-up operation and the pH detection are implemented. Then, it is determined based on the detected pH from the output of the pH sensor 61 whether or not the image pick-up operation of the examining target is completed. When it is determined that pH corresponds to that of a portion passing the examining portion (large intestine) (e.g., pH 6), the image pick-up operation and pH detection are stopped and the notifying means is started.

In this case, the notifying means notifying the completion of the image pick-up operation and pH detection by emitting light, has no notifying function in the body, but has a function for remarkably notifying it when the capsule is extracorporeally evacuated.

FIGS. 12A to 12G show typical examples of the operation in this case.

Referring to FIG. 12A, the switch 31 is turned on and then the mode enters a period for setting the operating mode.

At this period, referring to FIG. 12B, the user sets the sharing of the pH sensor 61 and operates the end of instruction. By this operation, referring to FIG. 12C, the capsule 3E operates in the observing mode. In this case, referring to FIG. 12D, the pH sensor 61 detects pH at a predetermined period in the observing mode, an output of the pH detection is sent to the processing circuit 27, and it is determined in the processing circuit 27 whether or not the sent pH is the predetermined pH.

Referring to FIG. 12E, when the sent pH is the predetermined pH, it is recognized that the image pick-up operation of the examined portion ends. Then, the operation in the observing mode ends at this timing and the mode enters a state of the operation in the notifying mode.

Referring to FIG. 12F, as a simpler method, the time for the image pick-up operation (medical action) in the observing mode is set by using the timer 27b. After the passage of the setting time, it is detected (determined or recognized) that the medical action is completed. Referring to FIG. 12G, the observing mode may end and the mode may be set to the notifying mode.

According to the third embodiment, upon ending the set medical action, the notifying means which facilitates the collection is started when the capsule is extracorporeally evacuated. Therefore, the collection is easily executed by using the notifying means.

According to the third embodiment, the optical observation is executed as the operating mode. However, the capsule can be applied to other medical actions such as ultrasonic observation, the pH monitoring, the drug application, and the syringe operation.

If the capsule can commonly be used for various medical actions, a product for various medical actions can be provided with low costs and it is advantageous for both a maker and a user.

In this case, the operating mode can be implemented for a long time depending on the medical action such as the pH detection using the pH sensor. In such a case, the original medical action may be performed in the operating mode and the mode for detecting the extracorporeal evacuation may commonly be used in the halfway.

In the case of examining the large intestine depending on the application, when the time interval to the extracorporeal evacuation after ending (completing) the medical action is short and then the scheduled time of the ending of the medical action is set by the timer 27b, considering the individual difference or variation, the capsule might extracorporeally be evacuated before the setting time of the timer 27b. Therefore, the capsule may be operated in the mode for detecting the extracorporeal evacuation of the capsule by using the sensor in the operating mode of the original medical action.

As a simple mode, the notifying means may be operated without using the sensor. In the case of flickering the LEDs as the notifying means, it is no problem for the patient that the capsule exists in the body. When the capsule is extracorporeally evacuated, it is easily understood by the flickering that the capsule is extracorporeally evacuated and the collection is easy.

According to the above-mentioned respective embodiments, in order to reduce the dirty state of the outer surface of the capsule and the scratch and to facilitate the cleaning and the treatment upon the collection, the water repellent processing (water repellent coating and processing for mixing a water repellent agent to a basic material) is performed for at least the side surface portion of the capsule exterior portion.

Further, the outer surface of the edge transparent cover may be mirror-finished (preferably, operating average roughness (Ra) 3.2a or less), and may be coated at least at the outer surface of the edge cover with the hardness higher than that of the material thereof.

According to the third embodiment, the capsule medical apparatus is not limited to that for the endoscopic observation or medical action using the image pick-up operation, and may widely be applied to the capsule medical apparatus for the ultrasonic diagnosis, drug application and syringe treatment.

As mentioned above, according to the first to third embodiments, the capsule medical apparatus is evacuated and then the notifying means notifies this information in association with the detection using the detecting means. Therefore, the capsule medical apparatus which is extracorporeally evacuated can easily be collected.

Next, a description is given of a capsule medical apparatus and a capsule medical apparatus collecting system capable of smooth collection, in which by detecting the state or position just before extracorporeally evacuating the capsule medical apparatus from the body, the collection of the capsule medical apparatus is prepared upon extracorporeally evacuating the capsule medical apparatus from the body, thereby smoothly collecting the capsule medical apparatus.

(Fourth Embodiment)

Hereinbelow, a description is given of a capsule medical apparatus and a capsule medical apparatus collecting system according to the fourth embodiment of the present invention with reference to FIGS. 13 to 16.

Figure 13:
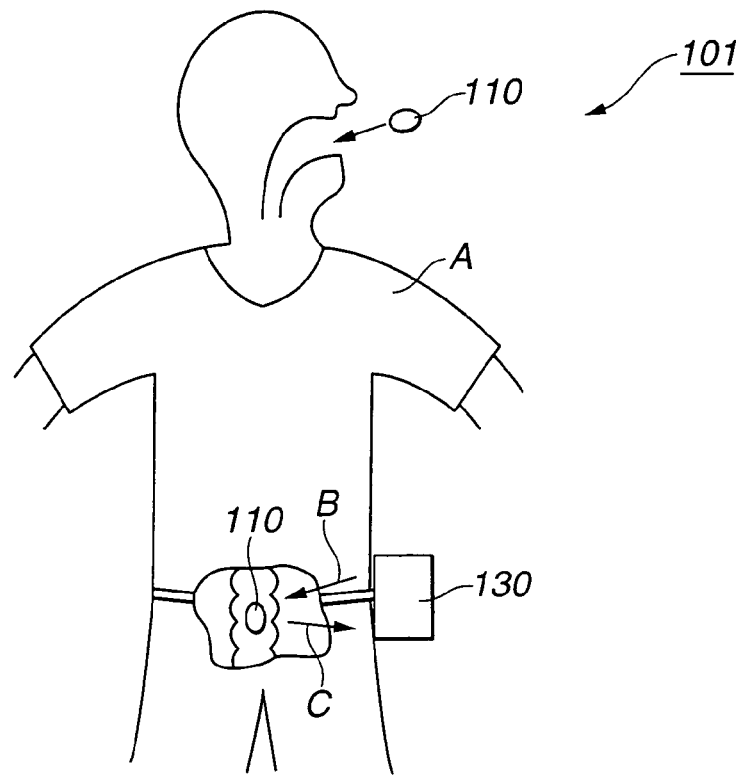
FIGS. 13 to 16 relate to a fourth embodiment of the present invention.

Referring to FIG. 13, a capsule endoscope collecting system (capsule medical apparatus collecting system) 101 according to the fourth embodiment comprises a capsule endoscope (capsule medical apparatus) 110 capable of being swallowed by a patient A and an extracorporeal device 130 which is extracorporeally arranged (to the body outside).

Figure 14:
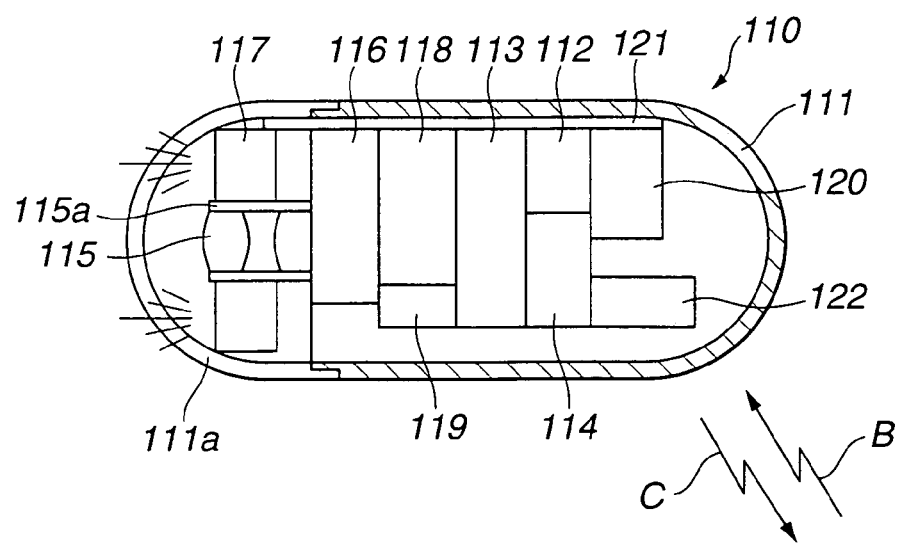

The capsule endoscope 110 passes through the body of the patient A (in the body) and detects the living body information. Referring to FIG. 14, the capsule endoscope 110 has a capsule container (casing) 111. The container 111 includes a receiving unit (detecting means) 112 such as a sensor which detects electric waves B at a predetermined frequency as position specifying information indicating the position of the container 111 that is extracorporeally supplied to the patient A, a determining unit (determining means) 113 which determined based on the electric waves B detected by the receiving unit 112 whether or not the container 111 is positioned in the large intestine, and a transmitting unit (notifying means) 114 which outputs a notifying signal C to outside the body (extracorporeally) when determining that the container 111 is positioned in the large intestine.

The receiving unit 112 has a function for detecting and receiving the electric waves B, for processing the received signal to a signal proportional to the level value of the electric waves B, and for transmitting the processed signal to the determining unit 113. The determining unit 113 has a function for comparing a threshold that is predetermined with a signal value transmitted by the receiving unit 112 and, when determining that the signal value is equal to the threshold or more, and for outputting an ON signal to the transmitting unit 114.

That is, when the capsule endoscope 110 is positioned in the large intestine (particularly, near the rectum), the distance to the extracorporeal device 130 is near and therefore the receiving unit 112 receives the electric waves B with a high output. Thus, the determining unit 113 determines whether or not the capsule endoscope 110 is positioned in the large intestine. The transmitting unit 114 has a function for outputting the notifying signal C when inputting the ON signal from the determining unit 113.

The container 111 has a transparent cover 111a at one end side and has a sealed structure. In addition to the above-mentioned components, the container 111 has another components. That is, in the transparent cover 111a, an objective lens 115 is attached to a lens frame 115a and an image pick-up element 116 for image pick-up operation such as a CMOS imager is arranged at the image forming position. White LEDs 117 are arranged as illuminating devices around the objective lens 115. Further, the image pick-up element 0.116 has, on the back side, a processing unit 118 which drives the white LEDs 117, drives the image pick-up element 116, and performs the processing of image pick-up data, and a memory 119 which stores the image picked up by the image pick-up element 116.

Further, the container 111 has a flexible printed-circuit board 121 connected to a battery 120. By electrically connecting the above-mentioned components to the flexible printed-circuit board 121, power necessary for the components is supplied thereto. An antenna 122 for receiving and transmitting signals to and from the extracorporeal device 130 is connected to the receiving unit 112 and the transmitting unit 114.

Figure 15:
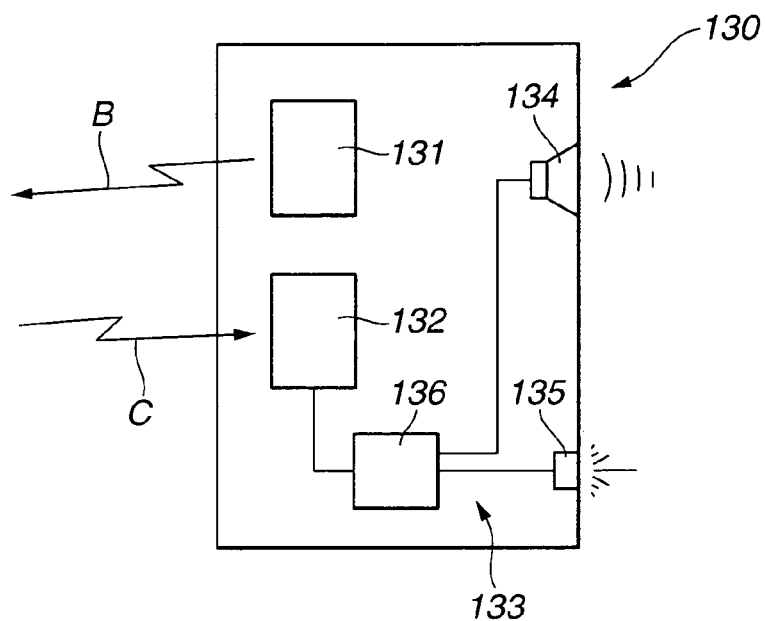

Referring to FIG. 15, the extracorporeal device 130 comprises a transmitting unit (supplying means) 131 for supplying, namely, transmitting the electric waves B, a receiving unit (receiving means) 132 for receiving the notifying signal C, and an output unit (output means) 133 for outputting sensible information based on the notifying signal C. The receiving unit 132 has a function for receiving the notifying signal C transmitted from the capsule endoscope 110 and for transmitting it to the output unit 133.

The output unit 133 has a processor 136 for outputting sensible sound and light from a speaker 134 and a light illuminating unit 135 upon receiving the notifying signal C transmitted from the speaker 134, the light illuminating unit 135, such as the LEDs, and the receiving unit 132. Thus, the patient A detects, as sound and light, that the capsule endoscope 110 is positioned in the large intestine.

Figure 16:
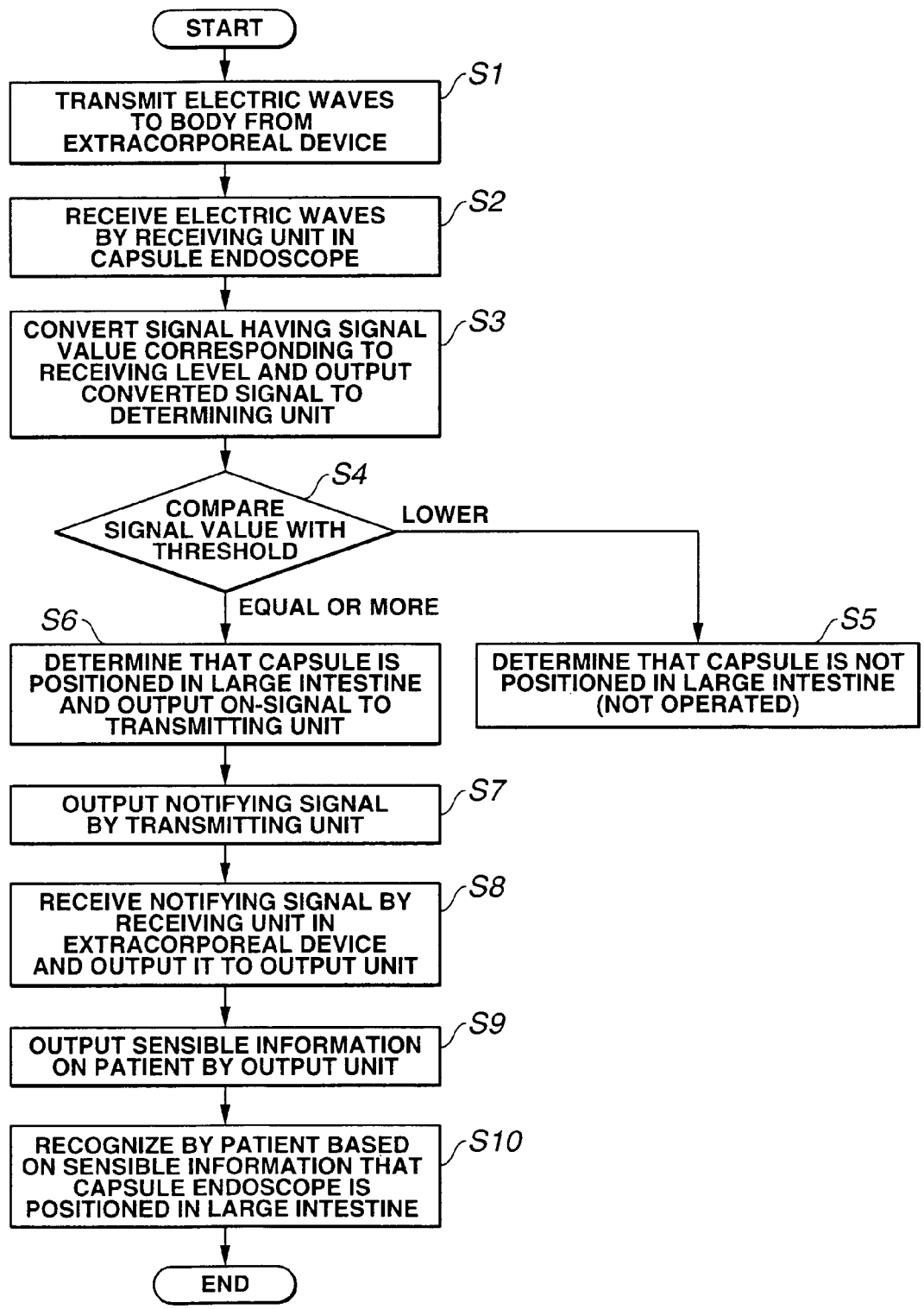

A description is given of the case of collecting the capsule endoscope 110 by the capsule endoscope collecting system 101 having the above structure with reference to FIG. 16.

As shown in FIG. 13, the patient A swallows the capsule endoscope 110 and put it in the body. The capsule endoscope 110 put in the body moves in the organ of digestion and, similarly therewith, illuminates the body by white LEDs 117 included in the container 111 as shown in FIG. 14, and periodically picks up the images of the body at a constant time interval by using the image pick-up element 116. The image pick-up data is subjected to predetermined processing by a processing unit 118, and is stored in a memory 119. As mentioned above, the capsule endoscope 110 detects the living body information at random and moves in the organ of digestion until it is administrated from the mouth and is evacuated.

Here, when the patient A senses the need to have a bowel movement or confirms that the capsule endoscope 110 has moved to the large intestine, as shown in FIG. 13, the extracorporeal device 130 is attached to a belt or the like. After attaching the extracorporeal device 130, the patient A turns on a switch (not shown) so as to transmit the electric waves B having a predetermined frequency to the body by using the transmitting unit 131 (S1).

The electric waves B are transmitted and, then, the receiving unit 112 in the capsule endoscope 110 receives the electric waves B via the antenna 122 (S2). The receiving unit 112 receives the electric waves B and, then, converts the received signal into a signal having a signal value corresponding to the receiving level, and outputs the converted signal to a determining unit 113 (S3). The determining unit 113 compares the transmitted signal value with a preset threshold (S4).

As a result of comparison, when the signal value is lower than the threshold (S5), the determining unit 113 determines that the capsule endoscope 110 has not moved to the large intestine. That is, when the capsule endoscope 110 has not moved to the large intestine or when it is in the initial stage that it exists in the large intestine but it might not be evacuated at the next bowel movement, the level of the electric waves B received by the receiving unit 113 is low and therefore the position of the capsule endoscope 110 can be determined.

When the signal value has the equal or more value as the threshold (S6), the determining unit 113 determines that the capsule endoscope 110 is positioned in the large intestine and outputs an ON signal to the transmitting unit 114. The ON signal is inputted and then the transmitting unit 114 extracorporeally outputs the notifying signal C via the antenna 122 (S7).

When the notifying signal C is outputted, the receiving unit 132 in the extracorporeal device 130 receives the notifying signal C and outputs it to the output unit 133 (S8). The notifying signal C is received and, then, the output unit 133 outputs the sound from the speaker 134 and/or light is illuminated from the light illuminating unit 135 so as to output sensible information for the patient A (S9).

Thus, the patient A easily senses by the sound or the light that the capsule endoscope 110 is positioned in the large intestine. The patient A recognizes the high possibility that the capsule endoscope 110 is evacuated at the next bowel movement (S10). Therefore, it is possible to prepare a collecting person (not shown) and properly prepare for using toilet dedicated for collection set in a hospital.

The capsule endoscope 110 evacuated from the patient A as scheduled is accurately collected and is examined. That is, examining information on body image pick-up data stored in the memory 119 is picked up and is examined.

As mentioned above, when it is determined that the signal value is lower than the threshold, the determining unit 113 does not transmit the notifying signal C to the extracorporeal device 130. Therefore, the sensible information such as the sound or light is not outputted. The patient A recognizes that the capsule endoscope 110 is not-positioned in the large intestine, the troublesomeness for unnecessary collecting preparation is prevented.

In the capsule endoscope collecting system 101 and the capsule endoscope 110, only by attaching the extracorporeal device 130 by the patient A, he can recognize, as the sensible information such as the sound or light, that the capsule endoscope 110 is positioned near the large intestine. That is, the capsule endoscope 110 compares the signal value of the electric waves B transmitted from the extracorporeal device 130 by the determining unit 113 with the preset threshold, thereby determining whether the capsule endoscope 110 is positioned in the large intestine with high accuracy.

When the capsule endoscope 110 is positioned in the large intestine, the notifying signal C is transmitted to the extracorporeal device 130 to notify the patient A of the sensible information. Therefore, as long as the patient A periodically attaches the extracorporeal device 130 or attaches the extracorporeal device 130 when he senses the need to have a bowel movement, he can easily recognize the high possibility that the capsule endoscope 110 is positioned in the large intestine and it is evacuated at the next bowel movement time. Therefore, the collecting preparation such as preparation of a collecting tool is efficiently performed. Vain collecting preparation is unnecessary every bowel movement and unnecessary troublesomeness is omitted.

According to the fourth embodiment, the position specifying information is the electric waves B having a predetermined frequency. However, it may be electric waves including a signal such as individual address information (ID) of the patient A. The position specifying information is not only the electric waves but also sound waves (low frequency and ultrasonic waves except for the audible sound), magnetic field, and strong light. In this case, the transmitting unit 131 in the extracorporeal device 130 and the receiving unit 112 in the capsule endoscope 110 can transmit and receive information corresponding to the position specifying information. Similarly, the determining unit 113 is set to compare the signal value with the threshold corresponding to the position specifying information. Further, the position specifying information may be transmitted from the capsule endoscope 110 and may be received by the receiving unit 132 in the extracorporeal device 130, and the extracorporeal device 130 may compare the receiving strength with the threshold and may determine whether or not the capsule endoscope 110 is positioned in the large intestine.

The extracorporeal device 130 is attached to the belt. However, the extracorporeal device 130 may be fixed near the rectum by using a specific holder, may be taken in a pocket, may be handled by the hand, and may be adhered and fixed to the buttock region by using a sticker.

Further, in the case of using the electric waves as the position specifying information, instead of the transmitting unit 131 in the extracorporeal device 130, an electronic device such as a mobile phone may transmit electric waves to the body.

(Fifth Embodiment)

Figure 17:
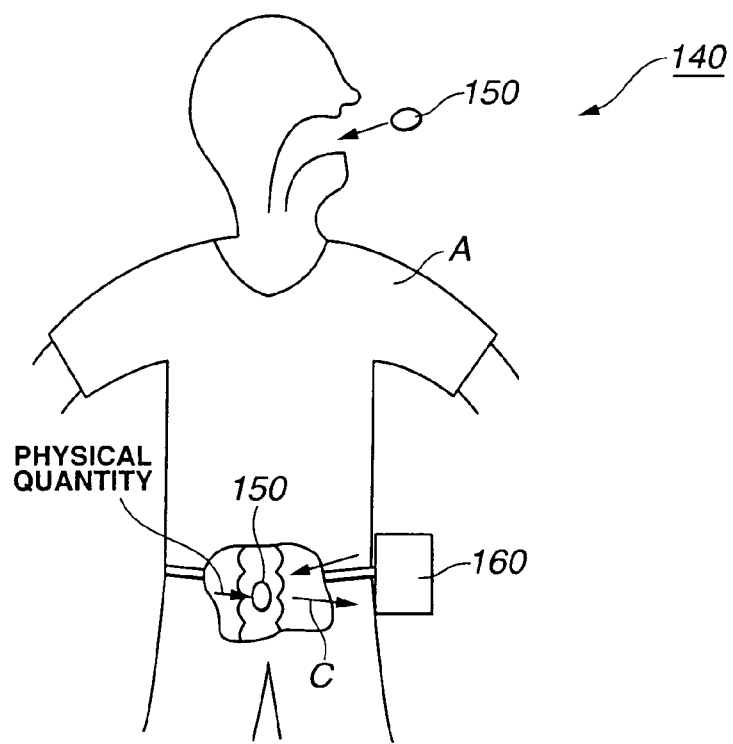
FIGS. 17 to 19 relate to a fifth embodiment of the present invention.
Figure 18:
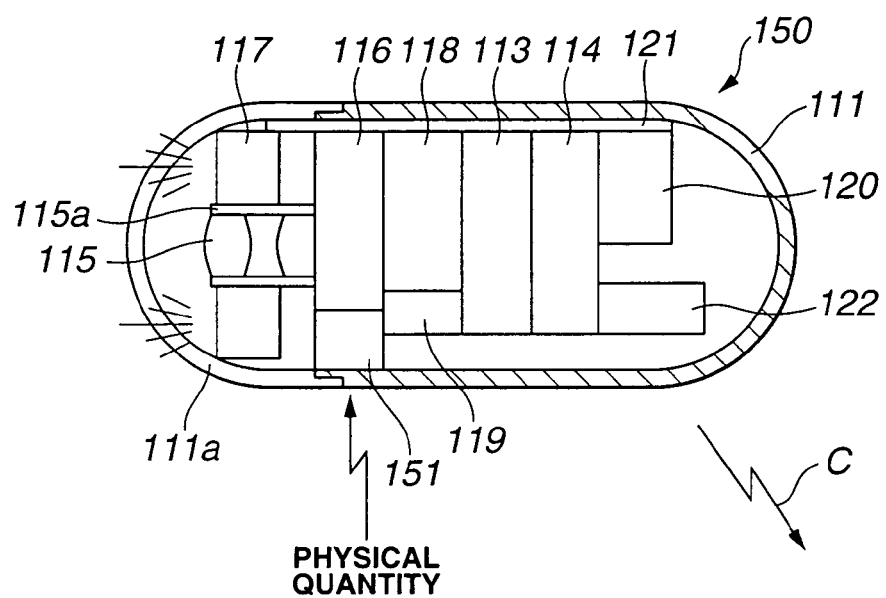

Next, a description is given of a capsule medical apparatus and a capsule medical apparatus collecting system according to the fifth embodiment of the present invention with reference to FIGS. 17 and 18. According to the fifth embodiment, the same components as those according to the fourth embodiment are designated by the same reference numerals and a description thereof is omitted.

According to the fourth embodiment, the position specifying information of the electric waves B is extracorporeally supplied, namely, from the extracorporeal device 130. Unlike the fourth embodiment, according to the fifth embodiment, the position specifying information is the physical quantity which is obtained from the large intestine in the living body.

Referring to FIG. 17, a capsule endoscope collecting system (capsule medical attachment collecting system) 140 according to the fifth embodiment comprises a capsule endscope (capsule endoscope apparatus) 150 and an extracorporeal device 160. Referring to FIG. 18, the capsule endoscope 150 has a chemical sensor 151 in the container (casing) 111. A part of the chemical sensor 151 is exposed to the outer surface of the container 111 and can detect the physical quantity such as chemical information on the outside of the container 111, such as a pH value, the absence or presence and the amount of characteristic materials such as microscopic organism, gene, and enzyme, and the concentration of marsh gas.

The chemical sensor 151 has a function for transmitting the physical quantity such as the detected pH value to the determining unit 113. The determining unit 113 compares the transmitted physical quantity with the preset threshold, thereby determining whether or not the capsule endoscope 150 is positioned in the large intestine. That is, the determining unit 113 previously sets, as the threshold, the pH value characteristic of the large intestine. According to the fifth embodiment, the capsule endoscope 150 does not have the above-mentioned receiving unit 112 in the container 111.

Figure 19:
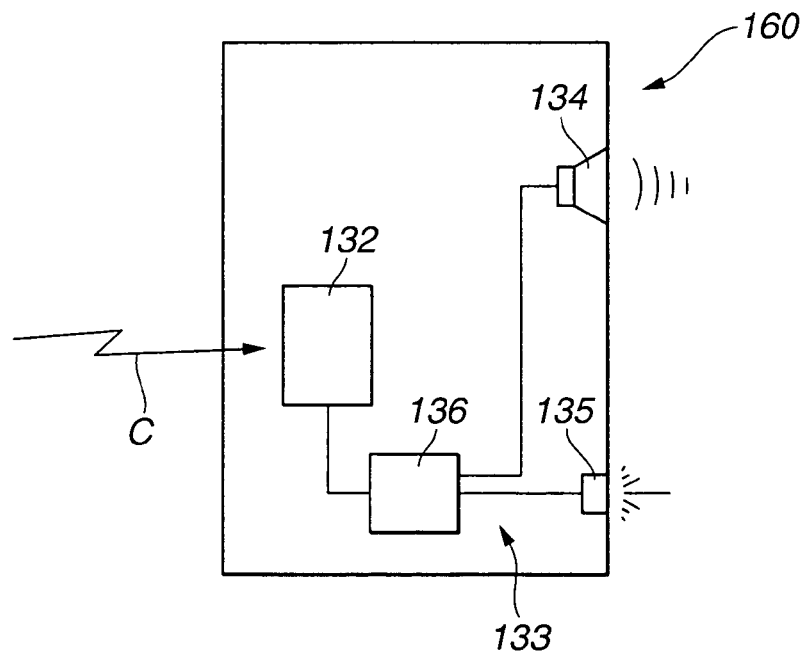

Referring to FIG. 19, the extracorporeal device 160 comprises a receiving unit (receiving means) 132 which receives the notifying signal C transmitted from the capsule endoscope 150, and an output unit (output means) 133 which outputs sensible information based on the notifying signal C.

A description is given of the case of collecting the capsule endoscope 150 by using the capsule endoscope collecting system 140 with the above-mentioned structure.

The capsule endoscope 150 given into the body moves the organ of digestion and reaches the large intestine, then, the chemical sensor 151 detects the pH value as the physical quantity characteristic of the large intestine and transmits the detected information to the determining unit 113. The determining unit 113 compares the transmitted pH value with the threshold. As a result of comparison, when the pH value is higher than the threshold, the determining unit 113 determines that the capsule endoscope 150 is positioned in the large intestine and outputs an ON signal to the transmitting unit 114.

Consequently, the transmitting unit 114 outputs the notifying signal C. The receiving unit 132 in the extracorporeal device 160 receives the outputted notifying signal C and the output unit 133 outputs the received signal to the patient A as the sensible information such as sound or light.

In the capsule endoscope collecting system 140 and the capsule endoscope 150, the determining unit 113 in the capsule endoscope 150 compares the physical quantity such as the pH value detected by the chemical sensor 151 with the preset threshold so as to determine whether the capsule endoscope 150 is positioned in the large intestine. That is, the determining unit 113 determines based on the physical quantity such as the pH value characteristic of the large intestine obtained by the chemical sensor 151 whether or not the capsule endoscope 150 is positioned in the large intestine. Therefore, the position of the capsule endoscope 150 in the large intestine can be determined with high possibility, can be notified to the extracorporeal device 160, and can be sensed by the patient A.

Only by periodically attaching the extracorporeal device 160 or attaching it when the patient A senses the need to have a bowel movement, it is possible to easily recognize the high possibility that the capsule endoscope 150 is positioned in the large intestine and is evacuated at the next bowel movement time. Thus, the collecting preparation such as the preparation for the collecting tool is efficiently performed.

According to the fifth embodiment, the chemical sensor 151 detects the physical quantity characteristic of the large intestine, e.g., the pH value, the presence or absence and amount of characteristic materials such as microscopic organism, gene, enzyme, and the concentration of marsh gas. Further, another physical quantity may be detected. For example, the impedance change may be detected in accordance with the presence or absence and amount of a solid material such as feces by providing an impedance sensor (sensor for measuring the resistance change by flowing constant current and measuring the voltage change). Furthermore, the pressure change characteristic of the large intestine may be detected by providing a pressure sensor which senses the pressure change on the exterior of the container, the color change characteristic of the large intestine may be detected by providing a color recognizing sensor, the sound characteristic of the large intestine such as the sound of urination and blood stream may be detected by providing a sound sensor such as a microphone or the like, or the capsule endoscope may be detected by measuring whether or not an acceleration sensor keeps at the same position at constant time.

(Sixth Embodiment)

Figure 20:
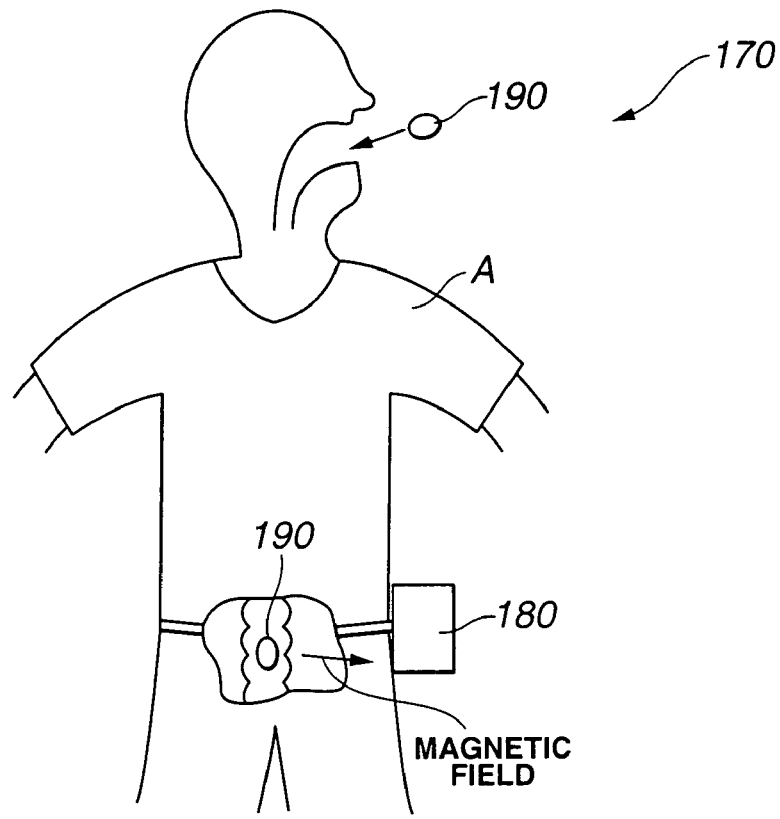
FIGS. 20 to 23 relate to a sixth embodiment of the present invention.
Figure 21:
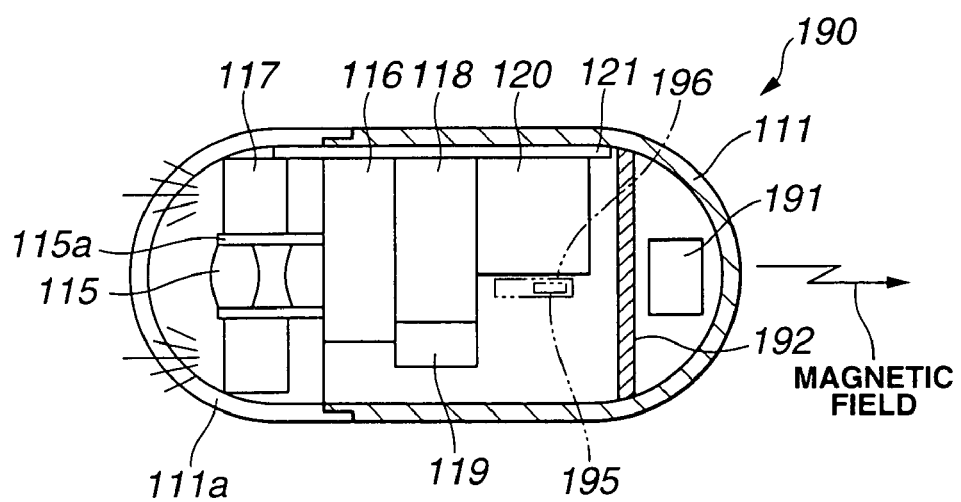

Next, a description is given of a capsule medical apparatus and a capsule medical apparatus collecting system according to the sixth embodiment of the present invention with reference to FIGS. 20 and 21.

According to the sixth embodiment, the same components as those according to the fourth embodiment are designated by the same reference numerals and a description thereof is omitted.

According to the fourth embodiment, the extracorporeal device outputs the position specifying information such as electric waves B to the capsule endoscope 110 and also outputs the sensible information to the patient A by receiving the notifying signal C from the capsule endoscope 110. On the other hand, according to the sixth embodiment, in a capsule endoscope collecting system (capsule medical apparatus collecting system) 170 according to the sixth embodiment, an extracorporeal device 180 determines the position of a capsule endoscope 190 based on the position specifying information of the magnetic field generated from the capsule endoscope (capsule medical apparatus) 190.

Referring to FIG. 20, the capsule endoscope collecting system 170 according to the sixth embodiment has a capsule endoscope (capsule medical apparatus) 190 and the extracorporeal device 180.

Referring to FIG. 21, the capsule endoscope 190 has a magneto (transmitting means) 191 which generates magnetic field extracorporeally detectable in the container 111.

The magneto 191 is partitioned by a non-magnetic partition so as to prevent the influence of the magnetic field to a memory 119 included in the container 111.

Figure 22:
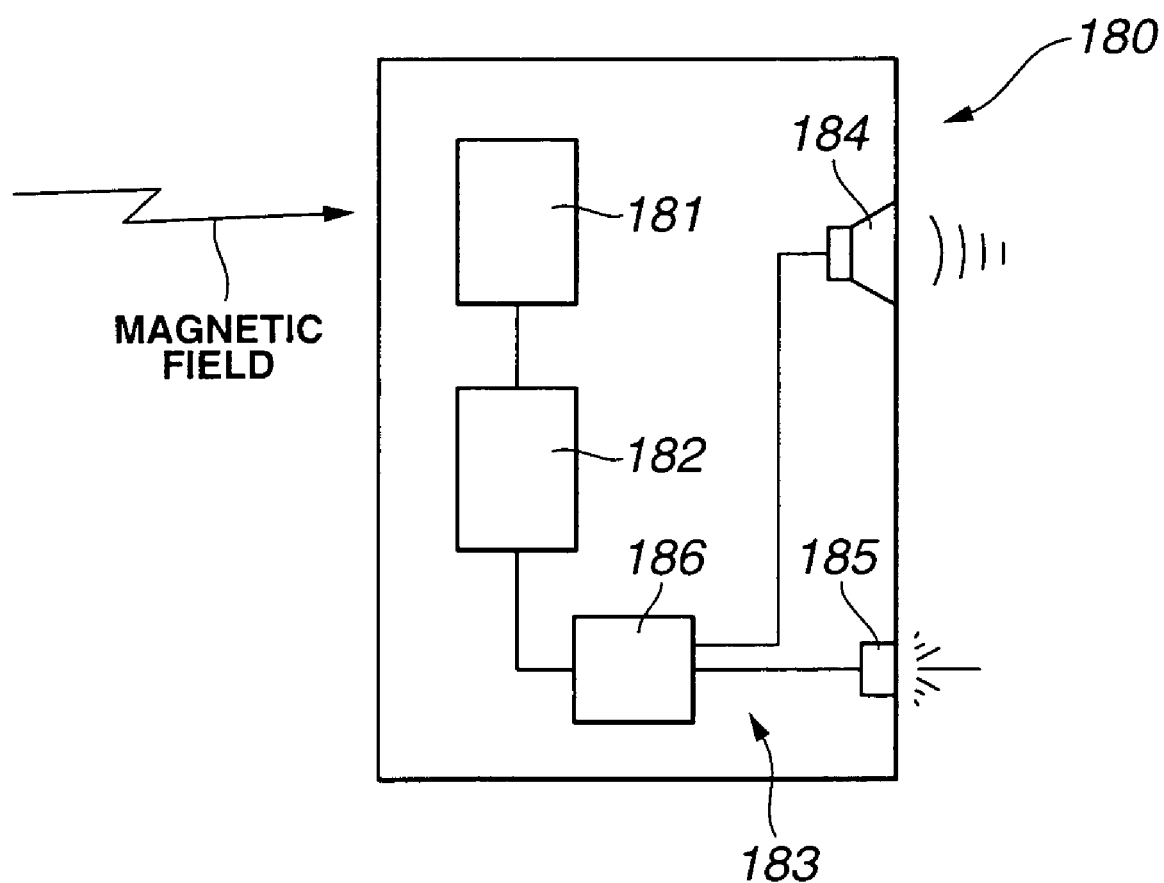

Referring to FIG. 22, the extracorporeal device 180 comprises a magnetic field receiving unit (receiving means) 181 which receives the magnetic field, a determining unit (determining means) 182 which determines based on the magnetic field received by the magnetic field receiving unit 181 whether or not the capsule endoscope 190 is positioned in the large intestine, and an output unit (output means) 183 which outputs the sensible information when the determining unit 182 determines that the capsule 190 is positioned in the large intestine.

That is, the magnetic field receiving unit 181 has a function for receiving and detecting the magnetic field and for transmitting a signal value corresponding to the magnetic field level to the determining unit 182. The determining unit 182 compares a preset threshold with the signal value transmitted from the magnetic field receiving unit 181. When the determining unit 182 determines that the signal value has the same value of the threshold or more, it has a function for transmitting an ON signal to the output unit 183.

That is, when the capsule endoscope 190 is positioned in the large intestine (particularly, near the rectum), since the distance between the capsule endoscope 190 and the extracorporeal device 180 is short, the magnetic field receiving unit 181 receives the magnetic field at the high level. Thus, the determining unit 182 determines whether or not the capsule endoscope 190 is positioned in the large intestine.

The output unit 183 has a processor 186 which outputs sensible sound and light from a speaker 184 and a light illuminating unit 185 upon receiving the ON-signal transmitted from the speaker 184, the light illuminating unit 185, such as LEDs, and determining unit 182. Thus, the patient A can recognize, as the sensible information such as sound and light, that the capsule endoscope 190 is positioned in the large intestine.

Figure 23:
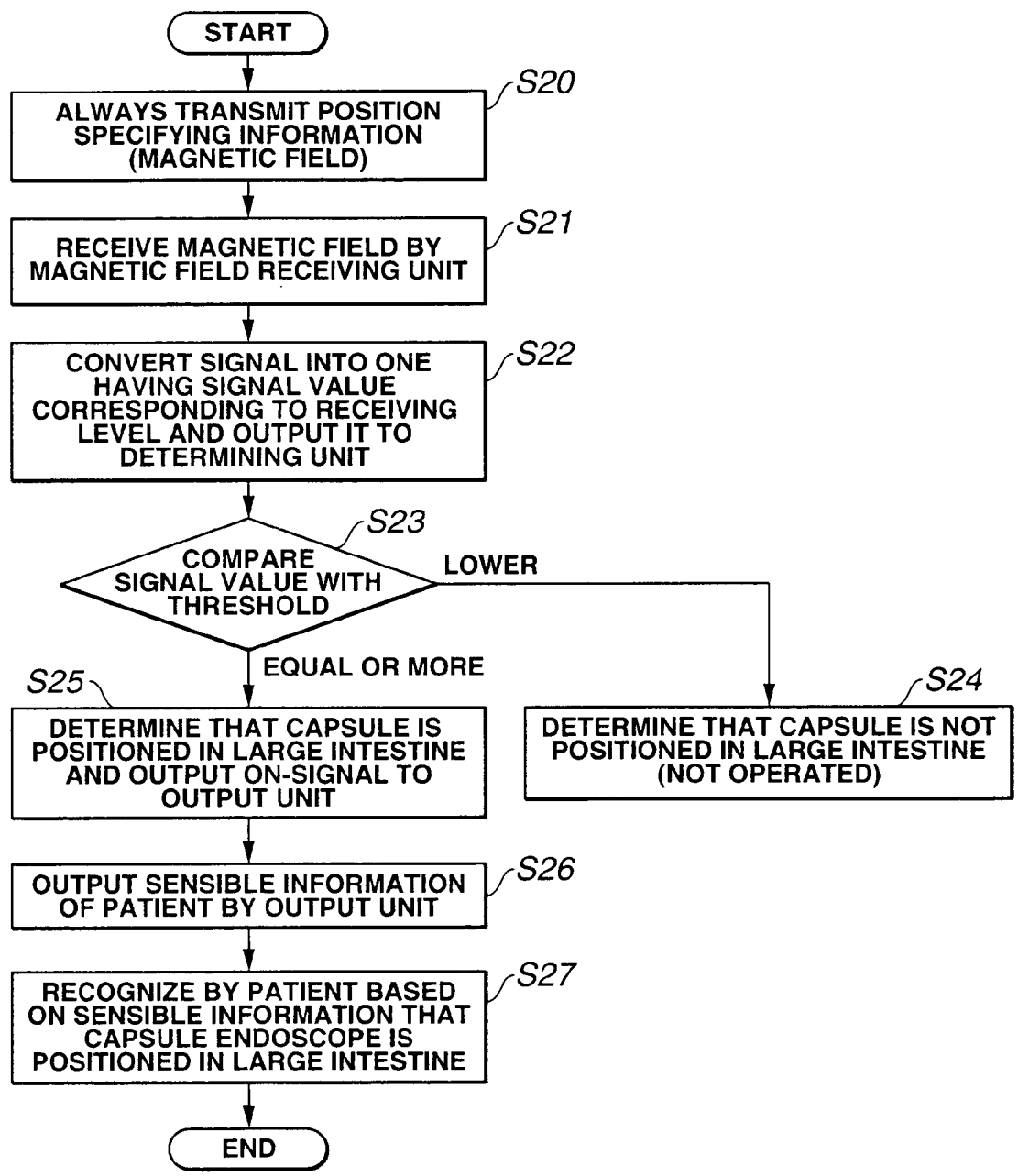

A description is given of the case of collecting the capsule endoscope 190 by the capsule endoscope collecting system 170 with the above-mentioned structure with reference to FIG. 23.

When the capsule endoscope 190 given in the body examines the body information and moves in the organ of digestion, the magneto 191 always generates, to the outside of the container 111, the magnetic field as the position specifying information (S20). When the patient A senses the need to have a bowel movement or wants to check whether or not the capsule endoscope 190 has already been moved to the large intestine, he attaches the extracorporeal device 180.

Upon attaching the extracorporeal device 180, the magnetic field receiving unit 181 receives the magnetic field generated from the capsule endoscope 190 (S21). The magnetic field receiving unit 181 receives the magnetic field, converts the received magnetic field into the signal value corresponding to the receiving level, and outputs the signal to the determining unit 182 (S22). The determining unit 182 compares the transmitted signal value with the preset threshold (S23).

As a result of comparison, when the signal value is lower than the threshold (S24), the determining unit 182 determines that the capsule endoscope 190 is not positioned in the large intestine. On the other hand, when the signal value has the same value as that of the threshold or more (S25), the determining unit 182 outputs the ON signal to the output unit 183. The output unit 183 receives the ON signal and, then, outputs the sensible information for the patient A by outputting the sound from the speaker 184 or illuminating the light from the light illuminating unit 185 (S26).

Thus, the patient A can easily sense by the sound or light that the capsule endoscope 190 is positioned in the large intestine. The patient A recognizes the high possibility that the capsule endoscope 190 is evacuated at the next bowel movement time (S27), he can properly prepare for a collecting tool (not shown) or for having a wash at a toilet dedicated for collection set in the hospital.

With the capsule endoscope collecting system 170 and the capsule endoscope 190, the capsule endoscope 190 always generates the magnetic field as the position specifying information and moves in the organ of digestion. The determining unit 182 in the extracorporeal device 180 can determine based on the magnetic field level received by the magnetic field receiving unit 181 whether or not the capsule endoscope 190 is positioned in the large intestine. When it is determined that the capsule endoscope 190 is positioned in the large intestine, the sensible information such as the sound or light can be outputted.

The patient A can easily recognize with high accuracy that the capsule endoscope 190 is positioned near the large intestine. Further, the patient A efficiently prepares for the collection of the capsule endoscope 190. Since the capsule endoscope 190 can notify its position only by providing the magneto 191 without the complicated structure, the size and costs are reduced and the patient A can easily swallow the capsule endoscope 190 and the passage of the capsule endoscope 190 through the body is improved.

According to the sixth embodiment, the position specifying information for notifying the position of the capsule endoscope 190 uses the magnetic field generated by the magneto 191. However, it is not limited to the magnetic field. For example, the position specifying information for notifying the position of the capsule endoscope 190 may be electric waves or ultrasonic waves. In this case, a receiving unit of the extracorporeal device may be set to receive the electric waves or ultrasonic waves in accordance with the position specifying information. Further, the position specifying information may use a radio IC chip or the like.

It is preferable to apply, as the radio IC chip, a micromini μ chip (having, e.g., the dimension of 0.4 mm in the vertical and horizontal directions and the thickness of 60 μm). Because the radio IC chip with the above-mentioned size does not influence on the size of the capsule endoscope 190.

In this case, information can be written and read between the capsule endoscope 190 and the extracorporeal device 180. Further, in the case of using the radio IC chip for the capsule endoscope 190, a patch antenna is used as receiving means of the extracorporeal device 180 and is adhered to the buttock region (near the anus). Particularly, a radio IC chip having an ID number is used to determine the position of the capsule endoscope 190 even when a plurality of capsule endoscopes 190 are used. Further, information such as a hit number may be written to the radio IC chip. FIG. 21 shows a radio chip 196 having an ID number 195 by an alternate long and two short dashes line. In the case of providing the radio IC chip 196, neither the magneto 191 nor the partition 192 is necessary. However, the capsule endoscope may be detected by using both the magneto 191 and partition 192 and the radio IC chip 196, which are different types.

The technical field of the present invention is not limited to the above embodiments and can variously be modified without departing from the essentials of the present invention.

For example, according to the embodiments, the capsule endoscope intermittently photographs the body intermittently and at random. However, the present invention is not limited to this and a capsule endoscope may continuously photograph the body by, e.g., a video camera. In this case, a video signal is stored.

Further, the examining information such as image pick-up data is stored in the memory. However, the image pick-up data may be transmitted to the extracorporeal device. In this case, the extracorporeal device may be set to have a function for receiving the examining information. Further, the capsule endoscope is not limited to one for photographing the body by a video camera or the like, so that another one that can detect the patient body information and transmit the data to the extracorporeal device may do. For example, the capsule endoscope may be a capsule medical apparatus for bleed detection, containing a hemoglobin sensor, and a capsule medical apparatus for examining body information such as the pH value, microscopic organism, and gene abnormality, which are intermittently obtained during a long time and transmitted to the extracorporeal device, and an ultrasonic capsule medical apparatus for intermittently obtaining an ultrasonic image and transmitting the obtained image to the extracorporeal device. Furthermore, the capsule endoscope may be a capsule medical apparatus which discharges drugs in the small intestine, or absorbs the body fluid.

According to the embodiments, as pre-processing, the faeces may be colored before a predetermined time of swallowing the capsule endoscope or a plurality of types of fine and bright particles which gleams mixed in the faeces may be swallowed. In this case, the color of faeces is changed or the fine and bright particles are mixed in the faeces, thereby determining the evacuation of the capsule endoscope. That is, the timing for needing the check-out using the extracorporeal device can be recognized.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A capsule medical apparatus comprising:
   a capsule adapted to be introduced into the body to perform medical actions;
   a detecting device provided in the capsule for detecting information of the living body;
   a determining device for determining whether the capsule has been evacuated from the body, the determining device comparing a value detected by the detecting device and a preset threshold value so as to determine whether the capsule has been evacuated from the body; and
   a notifying device for notifying that the capsule has been evacuated from the body in response to a determining result by the determining device.

2. A capsule medical apparatus according to claim 1, wherein the notifying device is a light emitting device provided in the capsule.

3. A capsule medical apparatus according to claim 1, wherein the notifying device is a vibrating device provided in the capsule.

4. A capsule medical apparatus according to claim 1, wherein the capsule stops performance of the medical actions in response to the actuation of the notifying device.

5. A capsule medical apparatus according to claim 1, wherein the capsule has an image pick-up device for picking up an image of a subject and an illuminating device for illuminating the subject.

6. A capsule medical apparatus according to claim 5, wherein the notifying device notifies that the capsule has been evacuated from the body by making the illuminating device emit light intermittently.

7. A capsule medical apparatus according to claim 5, wherein the capsule stops at least one of the actuations of the image pick-up device and the illuminating device in response to the actuation of the notifying device.

8. A capsule medical apparatus according to claim 1, wherein the capsule is capable of selectively switching between an operating mode to nullify the function of the detecting device and make effective the function to perform medical actions and a standby mode to make effective the function of the detecting device and stops performance of the medical actions.

9. A capsule medical apparatus according to claim 5, wherein the capsule is capable of selectively switching between an operating mode to nullify the detecting of information by the detecting device and make effective functions of the image pickup device and the illuminating device and a standby mode to make effective the detecting of information by the detecting device and stop at least one of the functions of the image pick-up device and the illuminating device.

10. A capsule medical apparatus according to claim 8, wherein the capsule switches between the operating mode and the standby mode at preset times.

11. A capsule medical apparatus according to claim 9, wherein the capsule switches between the operating mode and the standby mode at preset times.

12. A capsule medical apparatus according to claim 1, wherein the determining device compares the value detected by the detecting device and the preset threshold value so as to determine whether the capsule is at a position just before being evacuated from the body, and
   the notifying device notifies also in a case where the determining device has determined that the capsule is at a position just before being evacuated from the body.

* * * * *